(12) United States Patent
Miyazawa et al.

(10) Patent No.: US 7,781,452 B2
(45) Date of Patent: Aug. 24, 2010

(54) IMIDAZOPYRIDINE COMPOUND

(75) Inventors: Shuhei Miyazawa, Tsukuba (JP); Hitoshi Harada, Tsukuba (JP); Hideaki Fujisaki, Tsukuba (JP); Atsuhiko Kubota, Tsukuba (JP); Kotaro Kodama, Tsukuba (JP); Junichi Nagakawa, Tsukuba (JP); Kiyoshi Oketani, Tokyo (JP); Nobuhisa Watanabe, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 1013 days.

(21) Appl. No.: 11/385,786

(22) Filed: Mar. 22, 2006

(65) Prior Publication Data

US 2006/0167041 A1  Jul. 27, 2006

Related U.S. Application Data

(63) Continuation of application No. 11/110,756, filed on Apr. 21, 2005, now abandoned.

(30) Foreign Application Priority Data

Apr. 22, 2004  (JP) ............................ 2004-126533

(51) Int. Cl.
*A61K 31/444* (2006.01)
*C07D 471/02* (2006.01)

(52) U.S. Cl. ....................... 514/303; 546/118

(58) Field of Classification Search ................ 546/118; 514/303
See application file for complete search history.

(56) References Cited

U.S. PATENT DOCUMENTS

| 4,808,596 A | 2/1989 | Matsuishi et al. |
| 5,039,806 A | 8/1991 | Brandstram et al. |
| 5,430,042 A | 7/1995 | Lindberg et al. |
| 2004/0266828 A1 | 12/2004 | Garvey et al. |

FOREIGN PATENT DOCUMENTS

| EP | 0 187 977 A1 | 7/1986 |
| EP | 0 254 588 A1 | 1/1988 |
| JP | 59-181277 A | 10/1984 |
| JP | 62-207271 A | 9/1987 |
| JP | 63-146882 A | 6/1988 |
| JP | 1-190682 A | 7/1989 |
| JP | 2-22273 A | 1/1990 |
| JP | 5-117268 A | 5/1993 |
| JP | 5-507713 A | 11/1993 |
| WO | WO-91/17912 A1 | 12/1991 |
| WO | WO-00/50037 A1 | 8/2000 |
| WO | WO-2004/035020 A2 | 4/2004 |

OTHER PUBLICATIONS

Matsuishi et al. II, CA 112:77192 (1990).
N.J.V. Bell et al.; Appropriate Acid Suppression for the Management of Gastro-Oesophageal Reflux Disease; Digestion 1992; 51(supp 1): 59-67.
Vippagunta et al,. "Crystalline Solids," Advanced Drug Delivery Reviews, 48 (2001), 3-26.
Guillory, "Generation of Polymorphs, Hydrates, Solvates, and Amorphous Solids," in Brittain (ed.), Polymorphism in Pharmaceutical Solids, 95, Marcel Dekker, NY, 1999, 183-226.

*Primary Examiner*—Patricia L Morris
(74) *Attorney, Agent, or Firm*—Birch, Stewart, Kolasch & Birch, LLP

(57) ABSTRACT

A compound represented by the following general formula (1), or a salt or hydrate thereof:
[Formula 1]

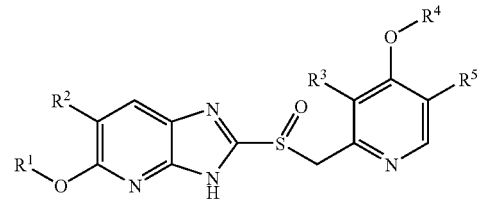

(1)

wherein $R^1$ represents a C1-C6 alkyl group or C2-C6 alkynyl group which may be substituted, or a phenyl group which may be substituted, $R^2$ represents a hydrogen atom or a C1-C6 alkyl group, $R^3$ represents methyl or ethyl group, $R^4$ represents a C1-C6 alkyl group, $R^5$ represents a hydrogen atom, provided that a compound wherein $R^1$ is a C1-C6 alkyl group unsubstituted or substituted with a halogen atom and $R^2$ is a hydrogen atom is excluded.

15 Claims, No Drawings

IMIDAZOPYRIDINE COMPOUND

CROSS-REFERENCE TO RELATED APPLICATIONS

The present application is a 37 C.F.R. §1.53(b) continuation of U.S. application Ser. No. 11/110,756 filed Apr. 21, 2005, now abandoned, which in turn claims priority on Japanese Application No. 2004-126533 filed Apr. 22, 2004. The entire contents of each of these applications is hereby incorporated by reference.

TECHNICAL FIELD

The present invention relates to an imidazopyridine compound useful as a gastric acid secretion inhibitor, or a salt thereof or a hydrate thereof.

The present invention also relates to an imidazopyridine compound useful as a therapeutic or preventive agent for acid related diseases (especially gastroesophageal reflux disease, symptomatic gastroesophageal reflux disease, gastric ulcer or duodenal ulcer), or a salt thereof or a hydrate thereof.

BACKGROUND ART

Peptic ulcer, such as gastric ulcer and duodenal ulcer, is considered to have developed as a result of self-digestion caused by imbalance between aggressive factors, such as acid and pepsin, and protective factors, such as mucus and blood.

The treatment of peptic ulcer is carried out by internal medicine in principle, and various drug treatments have been attempted. Particularly, drugs specifically inhibiting $H^+$-, $K^+$-ATPase, an enzyme present in gastric parietal cells and in charge of the final step of gastric acid secretion, suppressing the acid secretion and thereby preventing self-digestion, for example, omeprazole, esomeprazole, pantoprazole, lansoprazole, rabeprazole, etc., have been recently developed and clinically used.

Although these drugs have excellent therapeutic effects, drugs which have more long-lasting inhibitory effect on gastric acid secretion, higher safety and more suitable physicochemical stability are further required.

Compounds especially relevant to the present invention are described in the patent documents 1 to 3 but the specific compounds described in these patent documents and the specific compounds of the present invention are different in the chemical structure.

Patent Document 1 JP-A-62-207271
Patent Document 2 EP-A-0254588
Patent Document 3 EP-A-0187977

DISCLOSURE OF THE INVENTION

Problems to be Solved by the Invention

An object of the present invention is to provide a new compound having an excellent inhibitory effect on gastric acid secretion which is useful as a therapeutic or preventive agent for the treatment of acid related diseases.

Measures for Solving the Problems

The present inventors have conducted intensive studies for solving the above described problems, and as a result, have found that an imidazopyridine compound having a novel chemical structure has an excellent inhibition effect on gastric acid secretion and is useful as a therapeutic or preventive agent particularly for gastroesophageal reflux disease, symptomatic gastroesophageal reflux disease, gastric ulcer or duodenal ulcer, and thus completed the present invention.

That is, the present invention is directed to a compound having the following general formula (1), or a salt thereof or a hydrate thereof.

[Formula 1]

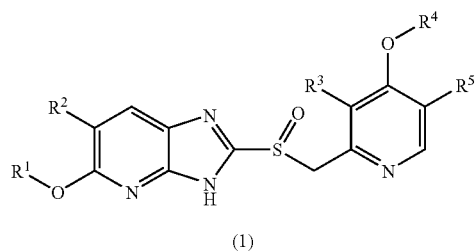

(1)

The present invention is also directed to a drug comprising the compound having the above described general formula (1), or a salt thereof or a hydrate thereof and a pharmaceutically acceptable carrier.

The present invention is further directed to a gastric acid secretion inhibitor comprising a compound having the above described general formula (1), or a salt thereof or a hydrate thereof.

The present invention is still further directed to a method using a compound of formula (1), or a therapeutic or preventive agent comprising a compound having the above described general formula (1), or a salt thereof or a hydrate thereof, for diseases caused by gastric acid, specifically, gastric ulcer, duodenal ulcer, stomal ulcer, gastroesophageal reflux disease, Zollinger-Ellison syndrome, symptomatic gastroesophageal reflux disease, endoscopy-negative gastroesophageal reflux disease, gastroesophageal regurgitation, paresthesia of pharyngolarynx, Barrett's esophagus, non-steroidal antiinflammatory drug (NSAID) ulcer, gastritis, stomach bleeding, gastrointestinal bleeding, peptic ulcer, bleeding ulcer, stress ulcer, gastric hyperacidity, dyspepsia, gastraparesis, senile ulcer, intractable ulcer, heartburn, bruxism, stomachache, heavy stomach, temporomandibular arthrosis or erosive gastritis. The method involves administering an effective amount of the compound or composition to a patient in need thereof.

Suitable examples of "acid related diseases" include, for example, gastric ulcer, duodenal ulcer, stomal ulcer, gastroesophageal reflux disease, Zollinger-Ellison syndrome or symptomatic gastroesophageal reflux disease, and more suitable examples include gastroesophageal reflux disease, symptomatic gastroesophageal reflux disease, gastric ulcer or duodenal ulcer, and still more suitable examples include (1) gastroesophageal reflux disease or symptomatic gastroesophageal reflux disease, or (2) gastric ulcers or duodenal ulcer.

In the meantime, the present invention is directed to a mono therapeutic or combination therapeutic agent for the eradication of *Helicobacter Pylori* comprising a compound having the above described general formula (1), or a salt thereof or a hydrate thereof.

Here, the above mentioned "preventive agent" includes an agent administered before onset of the disease, as well as a maintenance therapy agent or a relapse preventing agent after the disease is cured.

Further, the above mentioned "combination therapeutic agent for the eradication of *Helicobacter Pylori*" means a drug suitably adjusting the environment so that an eradicating agent, which is difficult to exhibit the effect under acidic condition, can exhibit its effect.

In the above described formula (1), $R^1$ represents a C1-C6 alkyl group which may have at least one substituent selected from the following α group, a C2-C6 alkenyl group, a C2-C6 alkynyl group, a C3-C6 cycloalkyl group, or a phenyl group which may have a substituent selected from the following β group;

$R^2$ represents a hydrogen atom or a C1-C3 alkyl group;

$R^3$ represents methyl or ethyl group;

$R^4$ represents a C1-C6 alkyl group;

$R^5$ represents a hydrogen atom;

α group represents a group consisting of a halogen atom, a C3-C6 cycloalkyl group, a phenyl group which may have at least one substituent selected from the following β group and a phenyloxy group which may have a substituent selected from the following β group;

β group represents a group consisting of a halogen atom and a C1-C6 alkoxy group;

provided that a compound wherein $R^1$ is a C1-C6 alkyl group unsubstituted or substituted with a halogen atom and $R^2$ is a hydrogen atom, or a salt thereof or a hydrate thereof are excluded from the present invention.

A "C1-C6 alkyl group" as used in this specification for convenience sake means a straight chain or branched chain alkyl group having 1 to 6 carbon atoms such as methyl, ethyl, n-propyl, isopropyl, n-butyl, isobutyl, s-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl or 2-ethylbutyl group.

A "C1-C3 alkyl group" as used in this specification for convenience sake means a straight chain or branched chain alkyl group having 1 to 3 carbon atoms such as methyl, ethyl, n-propyl or isopropyl.

A "C2-6 alkenyl group" as used in this specification for convenience sake means a vinyl group, allyl group, 1-propenyl group, isopropenyl group, 1-butenyl group, 2-butenyl group, 3-butenyl group, 1,3-pentadienyl group or 1,4-hexadienyl group.

A "C2-C6 alkynyl group" as used in this specification for convenience sake means an alkynyl group having 2 to 6 carbon atoms and 1 to 2 triple bonds such as ethynyl group, 1-propynyl group, 2-propynyl group, 2-butynyl group, 3-butynyl group, 1,3-pentadiynyl group, 1,4-hexadiynyl group, pentynyl group, or hexynyl group.

A "C3-6 cycloalkyl group" as used in this specification for convenience sake means a cyclopropyl group, cyclobutyl group, cyclopentyl group or cyclohexyl group.

A "halogen atom" as used in this specification for convenience sake means a fluorine atom, a chlorine atom, a bromine atom or an iodine atom.

A "C1-C6 alkoxy group" as used in this specification for convenience sake means a straight chain or branched chain alkoxy group having 1 to 6 carbon atoms such as methoxy, ethoxy, propoxy, isopropoxy, butoxy, isobutoxy, s-butoxy, t-butoxy, pentoxy, isopentoxy, 2-methylbutoxy, neopentoxy, hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy or 2,3-dimethylbutoxy group.

The expressions "which may be substituted" or "which may have at least one substituent" as used in this specification for convenience sake have the same meaning as "which may have one to three substituents at substitutable position(s) in any combination" unless the number of the substituent is particularly specified.

The expression "which is (are) substituted" as used in this specification for convenience sake has the same meaning as "which has (have) one to three substituents at substitutable position(s) in any combination" unless the number of the substituent(s) is particularly specified.

Preferably the above mentioned $R^1$ is an unsubstituted C1-C6 alkyl group, a C2-C6 alkynyl group or a C1-C6 alkyl group which may be substituted with halogen or a phenyl group which may have a substituent selected from the above described β group, and more preferably methyl group, 2,2,2-trifluoroethyl group, 2,2-difluoroethyl group, 2-(phenyl)propyl group, 2-(phenyloxy)ethyl group, 2-butynyl group, 3-fluorophenyl group, 4-fluorophenyl group or 4-methoxyphenyl group, and more preferably methyl group, 2,2,2-trifluoroethyl group or 2,2-difluoroethyl group, and most preferably methyl group.

Preferably, the above mentioned $R^2$ is a hydrogen atom, methyl group, ethyl group, or propyl group, and more preferably a hydrogen atom or methyl group.

The above mentioned $R^3$ is preferably a methyl group.

The above mentioned $R^4$ is preferably a methyl group.

Although the structural formula of a compound may represent a particular isomer in this specification for convenience sake, the present invention encompasses all the isomers including geometric isomers, optical isomers, stereoisomers and tautomer, and mixtures of isomers generated by the structure of the compound, and the compound is not limited to the particular formula described for convenience sake and may be either one of the isomer or a mixtures of isomers. Therefore, the compound of the present invention, which may be an optically active object and racemate, is not limited to a particular one and may include either one. Similarly, crystal polymorphism which may exist is not limited, and the crystal may comprise a single crystal form or may be a mixture, and the compound of the present invention may include an anhydride as well as a hydrate. Furthermore, so-called metabolite which is generated by the decomposition of Compound (1) of the present invention in a living body is also included by the present invention. Furthermore, the compound (so-called prodrug) which will lead to Compound (1) of the present invention through metabolism such as oxidization, reduction, hydrolysis and conjugation in a living body is also included by the present invention.

The compound of the present invention forms a salt in the above described general formula (1) at 1- or 3-position NH group in the imidazopyridine skeleton.

The "salt" is not particularly limited as long without any treatment is pharmacologically acceptable, and includes, for example, an inorganic base salt or an organic base salt.

Preferable examples of inorganic base salt include alkaline metal salts such as sodium salt and potassium salt, alkaline-earth-metals salts such as calcium salt or magnesium salt, aluminum salt or ammonium salt, and preferable examples of organic base salt include diethylamine salt, diethanolamine salt, meglumine salt or N,N'-dibenzylethylenediamine salt, etc.

Preferable compounds of the general formula (1) of the present invention include:

(2) compounds in which $R^1$ is an unsubstituted C1-C6 alkyl group, or a salt thereof or a hydrate thereof, (3) compounds in which $R^1$ is a C2-C6 alkynyl group, or a salt thereof or a hydrate thereof, (4) compounds in which $R^1$ is a C1-C6 alkyl group which may be substituted with halogen, or a salt thereof or a hydrate thereof, (5) compounds in which $R^1$ is a phenyl group which may have a substituent selected from the above described β group, or a salt thereof or a hydrate thereof, (6) compounds in which $R^1$ is methyl group, 2,2,2-trifluoroethyl group, 2,2-difluoroethyl group, 2-(phenyl)propyl group, 2-(phenyloxy)ethyl group, 2-butynyl group, 3-fluorophenyl group, 4-fluorophenyl group or 4-methoxyphenyl group, or a salt thereof or a hydrate thereof, (7) compounds in which $R^1$ is methyl group, 2,2,2-trifluoroethyl group or 2,2-difluoroethyl group, or a salt thereof or a hydrate thereof, (8) compounds in which $R^2$ is a hydrogen atom, methyl group, ethyl group, or a propyl group, or a salt thereof or a hydrate thereof, (9) compounds in which $R^2$ is methyl group, or a salt thereof or a hydrate thereof,

(10) compounds in which $R^2$ is a hydrogen atom, or a salt thereof or a hydrate thereof,

(11) compounds in which $R^3$ is methyl group, or a salt thereof or a hydrate thereof, or

(12) compounds in which $R^4$ is methyl group, or a salt thereof or a hydrate thereof.

Furthermore, compounds obtained by selecting $R^1$ from the above (2), (3), (4), (5), (6) or (7), $R^2$ from the above (8), (9) or (10), $R^3$ from the above (11) or $R^4$ from the above (12) in any combination, or a salt thereof or a hydrate thereof are also preferable.

Preferable compounds among the specific compounds of the present invention, or a salt thereof or a hydrate thereof are 5-methoxy-2-(((4-methoxy-3-methyl-2-pyridinyl)methyl)sulfinyl)-6-methyl-3H-imidazo[4,5-b]pyridine, 2-(((4-methoxy-3-methyl-2-pyridinyl)methyl)sulfinyl)-6-methyl-5-(2,2,2-trifluoroethoxy)-3H-imidazo[4,5-b]pyridine, or 5-(2,2-difluoroethoxy)-2-(((4-methoxy-3-methyl-2-pyridinyl)methyl)sulfinyl)-6-methyl-3H-imidazo[4,5-b]pyridine, or a salt thereof or a hydrate thereof (especially a sodium salt thereof).

EFFECT OF THE INVENTION

Since the compound of the present invention has excellent gastric acid secretion inhibitory activity, more sustainable gastric acid secretion inhibitory activity, higher safety (for example, causing less induction of cytochrome P450) and more suitable physicochemical stability, it is useful as a pharmaceutical agent, particularly a therapeutic or preventive agent for acid related diseases and a mono therapeutic or combination therapeutic agent for the eradication of *Helicobacter Pylori*.

BEST MODE FOR CARRYING OUT THE INVENTION

The compound of the present invention can be produced by the process indicated below. However, process for producing the compound the present invention is not limited thereto.

Compound (1) of the present invention can be produced by the following Process A.

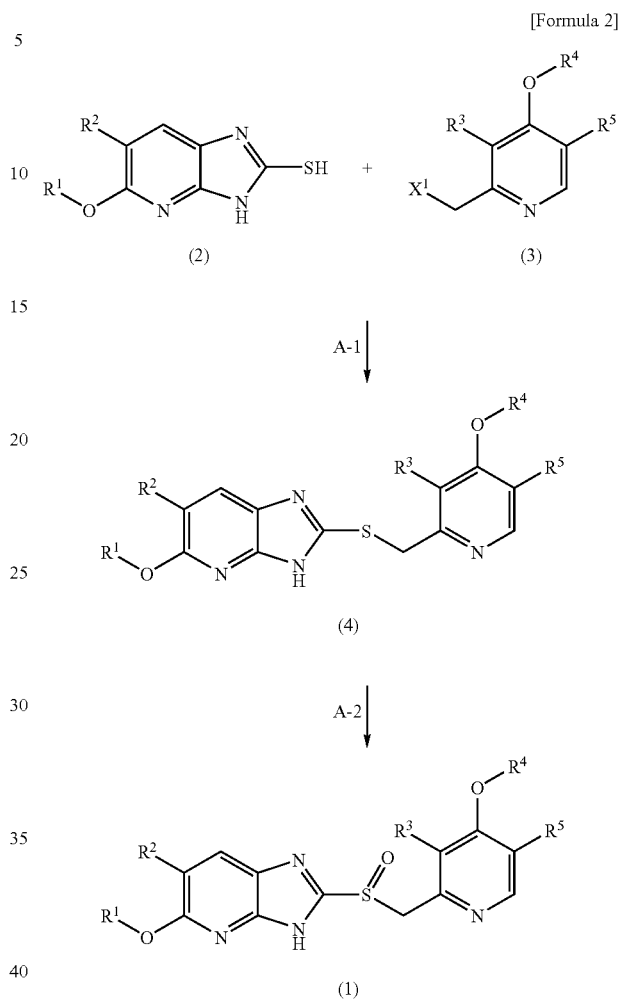

In the above scheme, $R^1$, $R^2$, $R^3$, $R^4$ and $R^5$ represent the same as defined above, and $X^1$ represents a leaving group and is preferably an alkylsulfonyloxy group which may be substituted or a benzenesulfonyloxy group which may be substituted (for example, methanesulfonyloxy, ethanesulfonyloxy, benzenesulfonyloxy, p-toluenesulfonyloxy group, etc.) or a chlorine atom, a bromine atom or an iodine atom, and more preferably a chlorine atom and a methanesulfonyloxy group.

Hereafter, each step of Process A method is explained.

(Step A-1) Thioetherification

This step is a step where Compound (2) and Compound (3) or a salt thereof (particularly, a hydrochloride salt) is made to react in the presence or absence of a base, in the absence of a solvent or in an inert solvent to produce Compound (4).

As Compound (4a), a commercially available compound or a compound synthesized based on a process known by publication can be used.

The usable solvent is not particularly limited as long as it can dissolve the starting materials to some extent and does not inhibit the reaction, and includes, for example, alcohols such as methanol, ethanol, n-propanol, isopropanol, n-butanol, isobutanol, t-butanol, isoamyl alcohol, diethylene glycol, glycerin, octanol, cyclohexanol and methyl cellosolve; halogenated hydrocarbons such as chloroform, dichloromethane, 1,2-dichloroethane and carbon tetrachloride; ethers such as diethyl ether, diisopropyl ether, tetrahydrofuran, dioxane, dimethoxyethane, diethylene glycol dimethyl ether; N,N-dimethylformamide; dimethylsulfoxide; water; or mixtures of these solvents, and is preferably alcohols and most preferably methanol.

The usable base includes, for example, inorganic bases such as sodium hydride, potassium hydride, lithium carbonate, sodium carbonate, potassium carbonate, lithium hydroxide, sodium hydroxide, potassium hydroxide; and organic bases such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethyl aniline, N,N-diethylaniline, 1,5-diazabicyclo[4.3.0]nona-5-ene (DBN), 1,4-diazabicyclo[2.2.2]octane (DABCO), 1,8-diazabicyclo[5.4.0]undeca-7-ene (DBU), and is preferably inorganic bases such as sodium hydride, potassium hydride, lithium hydroxide, sodium hydroxide, potassium hydroxide, and most preferably sodium hydroxide.

Although the reaction temperature may vary depending on starting materials, solvent and base catalyst, it is typically 0 to 100° C., and is preferably 10 to 40° C.

Although the reaction time may vary depending on starting materials, solvent, base catalyst and reaction temperature, it is typically 30 minutes to 20 hours, and is preferably 1 to 8 hours.

(Step A-2) Oxidation Reaction

This step is a step where an oxidizing reagent is made to react with Compound (4) in the absence of a solvent or in an inert solvent to produce Compound (1) of the present invention.

The usable solvent is not particularly limited as long as it can dissolve the starting materials to some extent and does not inhibit the reaction, and includes, for example, alcohols such as methanol, ethanol, n-propanol, isopropanol, n-butanol, isobutanol, t-butanol, isoamyl alcohol, diethylene glycol, glycerin, octanol, cyclohexanol and methyl cellosolve; aromatic hydrocarbons such as benzene, toluene; halogenated hydrocarbons such as chloroform, dichloromethane, 1,2-dichloroethane and carbon tetrachloride; amides such as formamide, N,N-dimethylformamide, N,N-dimethylacetamide, hexamethylphosphoric triamide, and is preferably an aromatic hydrocarbon, an alcohol or a mixture of these solvents, and most preferably is a mixture of toluene and methanol, or dichloromethane.

The usable oxidizing reagent includes, for example, aqueous hydrogen peroxide solution, t-butyl hydroperoxide, sodium periodate, peracetic acid, perbenzoic acid, metachloroperbenzoic acid, urea-hydrogen peroxide addition compound (($NH_2$)$_2$CO.$H_2O_2$), etc., and it is preferably metachloroperbenzoic acid. When performing asymmetric oxidation, a commonly used asymmetric oxidizing agent can also be used.

Although the reaction temperature may vary depending on starting materials, solvent, and oxidizing reagents, typically, it is −100 to 100° C., and preferably −70 to 70° C.

Although the reaction time may vary depending on starting materials, solvent, oxidizing reagent and reaction temperature, it is typically 30 minutes to 24 hours, and is preferably 1 to 5 hours.

The compound obtained above can be converted to a salt by an ordinary method. For example, a base is made to react with Compound (1) in the absence of a solvent or in an inert solvent. An alcohol such as methanol or ethanol, water or a mixture of these solvents, preferably a mixture of ethanol and water is used as a solvent, and an alkaline metal hydroxide such as sodium hydroxide and potassium hydroxide, an alkaline-earth-metals hydroxide such as magnesium hydroxide, an alkoxide such as sodium methoxide, sodium t-butoxide and magnesium methoxide, preferably sodium hydroxide, is used as a base in an aqueous solution. Typically, the reaction temperature is −50 to 50° C., and is preferably 10 to 40° C. Typically, the reaction time is 5 minutes to 2 hours, and is preferably 10 to 30 minutes.

Compound (2) and compound (3) which are intermediates in the above described Process A may be commercial products or easily produced from commercial products by a process which those skilled in the art usually employs, and they can also be produced by Processes B, C, D or E described below.

Compound (2) can be produced by the following Process B.

Process B

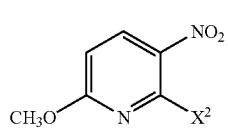

[Formula 3]

(4a)

↓ B-7

-continued

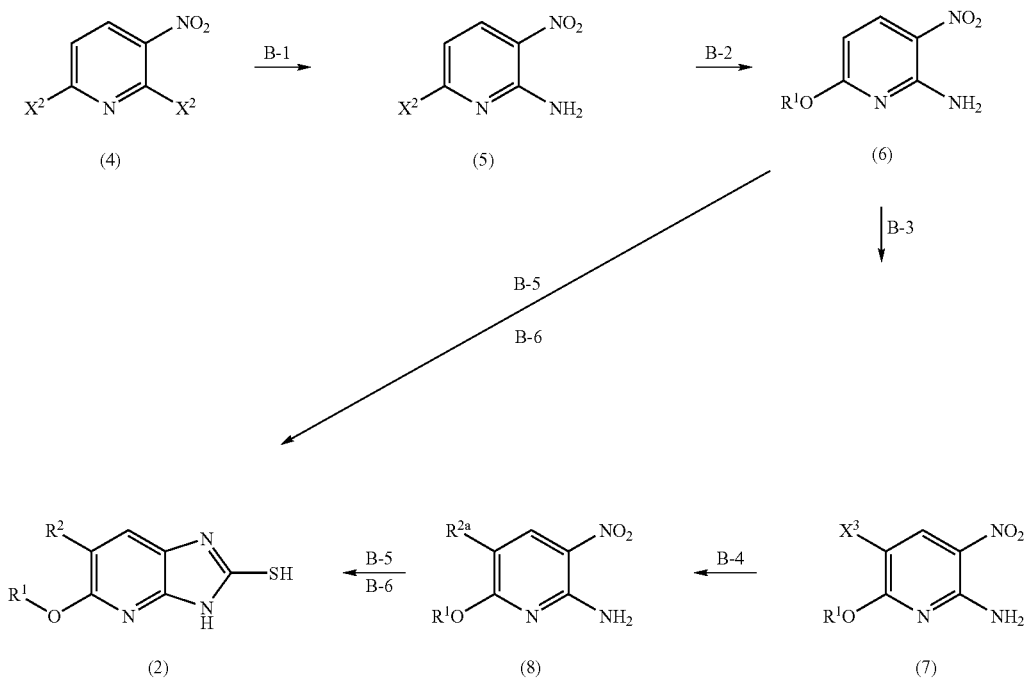

In the above scheme, $R^1$ and $R^2$ represent the same as defined above, and $R^{2a}$ represents a methyl group, vinyl group or allyl group, and $X^2$ represents a leaving group, preferably a chlorine atom, a bromine atom or an iodine atom, and more preferably a chlorine atom. $X^3$ represents a leaving group, preferably a chlorine atom, a bromine atom or an iodine atom, and more preferably an iodine atom.

Hereafter, each step of the Process B is explained.

(Step B-1) Amination Reaction

This step is a step where ammonia is made to react with Compound (4) in the presence or absence of an alkaline metal carbonate, in the absence of a solvent or in an inert solvent, to produce Compound (5).

The usable solvent is not particularly limited as long as it can dissolve the starting materials to some extent and does not inhibit the reaction, and includes, for example, aliphatic hydrocarbons such as hexane, heptane, ligroin, petroleum ether; halogenated hydrocarbons such as chloroform, dichloromethane, 1,2-dichloroethane, carbon tetrachloride; ethers such as diethyl ether, diisopropyl ether, tetrahydrofuran, dioxane, dimethoxyethane, diethylene glycol dimethyl ether; amides such as formamide, N,N-dimethylformamide, N,N-dimethylacetamide, hexamethylphosphoric triamide; t-butyl alcohol, water, etc., and is preferably a mixture of t-butyl alcohol and water or a mixture of N,N-dimethylformamide and water.

The usable alkaline metal carbonate includes, for example, sodium carbonate, potassium carbonate, sodium bicarbonate, potassium bicarbonate, etc., and is preferably potassium carbonate.

Although the reaction temperature may vary depending on starting materials, solvent, and alkaline metal carbonate, it is typically 0 to 100° C., and is preferably 40 to 80° C.

Although the reaction time may vary depending on starting materials, solvent, alkaline metal carbonate, and reaction temperature, it is typically 6 to 48 hours and is preferably 12 to 36 hours.

As Compound (4), a commercially available compound or a compound synthesized according to any process known by publication can be used.

(Step B-2) $R^1$—O Group Introducing Reaction

Reaction conditions may be changed depending on the type of $R^1$—OH.

a) In the case that $R^1$—OH is an alcohol:

This step is a step where Compound (5) and alcohol $R^1$—OH (wherein $R^1$ represent the same as defined above) are made to react in the presence of a base in the absence of a solvent or in an inert solvent to produce Compound (6).

The usable solvent is not particularly limited as long as it can dissolve the starting materials to some extent and does not inhibit the reaction, and includes, for example, alcohols which form the desired $R^1$—O— such as methanol and ethanol; aliphatic hydrocarbons such as hexane, heptane, ligroin, petroleum ether; halogenated hydrocarbons such as chloroform, dichloromethane, 1,2-dichloroethane, carbon tetrachloride; aromatic hydrocarbons such as benzene, toluene; ethers such as diethyl ether, diisopropyl ether, tetrahydrofuran, dioxane, dimethoxyethane, diethylene glycol dimethyl ether; amides such as formamide, N,N-dimethylformamide, N,N-dimethylacetamide, hexamethylphosphoric triamide, N-methylpyrrolidone; dimethylsulfoxide, water, or a mixture of these solvents, and is preferably dimethylsulfoxide, ether or amide, and most preferably, tetrahydrofuran when $R^1$—OH is primary alcohol, and dimethylsulfoxide or N-methylpyrrolidone in the case of secondary alcohol.

The usable base includes, for example, alkaline metal carbonates such as lithium carbonate, sodium carbonate, potassium carbonate; alkaline metal hydroxides such as lithium hydroxide, sodium hydroxide, potassium hydroxide; metal alkoxides such as lithium methoxide, sodium methoxide, sodium ethoxide, potassium-t-butoxide; alkaline metal hydrides such as sodium hydride, potassium hydride; alkaline metal alkoxides prepared from alkaline metals; n-butyl lithium, lithium diisopropylamide, etc., and it is preferably an alkaline metal hydride and most preferably sodium hydride.

Although the reaction temperature may vary depending on starting materials, solvent, and bases, it is typically 0 to 100° C., and when $R^1$—OH is a primary alcohol, it is 10 to 40° C., and in the case of secondary alcohol, it is 50 to 100° C.

Although the reaction time may vary depending on starting materials, solvent, base, and reaction temperature, it is typically 6 to 48 hours and is preferably 12 to 24 hours.

b) In the case that $R^1$—OH is a phenol

This step is a step where Compound (5) and a phenol $R^1$—OH (wherein $R^1$ represent the same as defined above) are made to react in the presence of a palladium catalyst, ligand, and an alkaline metal phosphate in the absence of a solvent or in an inert solvent to produce Compound (6).

The usable solvent is not particularly limited as long as it can dissolve the starting materials to some extent and does not inhibit the reaction, and includes, for example, alcohols such as methanol, ethanol, n-propanol, isopropanol, n-butanol, isobutanol, t-butanol, isoamyl alcohol, diethylene glycol, glycerin, octanol, cyclohexanol and methyl cellosolve; aliphatic hydrocarbons such as hexane, heptane, ligroin, petroleum ether; ethers such as diethyl ether, tetrahydrofuran, dioxane, dimethoxyethane, diethylene glycol dimethyl ether; halogenated hydrocarbons such as chloroform, dichloromethane, 1,2-dichloroethane and carbon tetrachloride; aromatic hydrocarbons such as benzene, toluene; amides such as formamide, N,N-dimethylformamide, N,N-dimethylacetamide, hexamethylphosphoric triamide; organic acids such as acetic acid, etc., and is preferably an aromatic hydrocarbon and most preferably toluene.

The usable palladium catalyst includes, for example, a palladium catalyst such as tetrakis(triphenylphosphine)palladium(0), tris(dibenzylideneacetone)dipalladium(0), bis(dibenzylideneacetone)palladium(0), bis(tri-t-butylphosphine)palladium(0), palladium black; a palladium catalyst precursor (which generates a palladium catalyst within a system) such as dichlorobis(triphenylphosphine)palladium(II), palladium(II) acetate, 1,1'-bis(diphenylphosphino)ferrocenedichloropalladium(II), dichlorobis(tri-o-tolylphosphine)palladium(II), dichlorobis(tricyclohexylphosphine)palladium(II) etc., and is preferably palladium(II) acetate.

The usable ligand includes, for example, triphenylphosphine, tri-t-butylphosphine, tri(4-methylphenyl)phosphine, 2-(di-t-butylphosphino)biphenyl, 2-(dicyclohexylphosphino)biphenyl, tricyclohexylphosphine, 1,1'-bis(diphenylphosphino)ferrocene, di-t-butylphosphoniumtetrafluoroborate, etc., and is preferably 2-(di-t-butylphosphino)biphenyl.

The usable alkaline metal phosphate includes, for example, sodium phosphate, potassium phosphate, etc., and is preferably potassium phosphate.

Although the reaction temperature may vary depending on starting materials, solvent, palladium catalysts, etc., it is typically 50 to 200° C., and preferably 120 to 180° C.

Although the reaction time may vary depending on starting materials, solvent, palladium catalyst, reaction temperature, etc., it is typically 6 to 48 hours and is preferably 12 to 24 hours.

(Step B-3) Halogenation Reaction (Represented by Bromination and an Iodization Reaction)

This step is a step where a brominating agent or an iodizing agent is made to react with Compound (6) in the absence of a solvent or in an inert solvent to produce Compound (7).

The usable solvent is not particularly limited as long as it can dissolve the starting materials to some extent and does not inhibit the reaction, and includes, for example, alcohols such as methanol, ethanol, n-propanol, isopropanol, n-butanol, isobutanol, t-butanol, isoamyl alcohol, diethylene glycol, glycerin, octanol, cyclohexanol, methyl cellosolve; aliphatic hydrocarbons such as hexane, heptane, ligroin, petroleum ether; halogenated hydrocarbons such as chloroform, dichloromethane, 1,2-dichloroethane and carbon tetrachloride; ethers such as diethyl ether, diisopropyl ether, tetrahydrofuran, dioxane, dimethoxyethane, diethylene glycol dimethyl ether; nitrile such as acetonitrile; amides such as formamide, N,N-dimethylformamide, N,N-dimethylacetamide and hexamethylphosphoric triamide; organic acids such as acetic acid, etc., and it is preferably acetonitrile, an alcohol (particularly methanol) or an organic acid and most preferably acetic acid or acetonitrile.

The usable brominating or iodizing agent includes, for example, bromine ($Br_2$), iodine ($I_2$), N-bromosuccinimide, N-iodosuccinimide, etc., and is preferably N-iodosuccinimide or N-bromosuccinimide.

Although the reaction temperature may vary depending on starting materials, solvent, brominating or iodizing agent, it is typically 0 to 60° C., and preferably 10 to 40° C.

Although the reaction time may vary depending on starting materials, solvent, brominating agent or iodizing agent, reaction temperature, etc., it is typically 2 to 24 hours and preferably 5 to 24 hours.

(Step B-4) Alkylation or Alkenylation Reaction (1) In the case that $R^{2a}$ is methyl group This step is a step where Compound (7) and a desired trialkylboroxin are made to react in the presence of a palladium catalyst and a base in the absence of a solvent or in an inert solvent to produce Compound (8).

The usable solvent is not particularly limited as long as it can dissolve the starting materials to some extent and does not inhibit the reaction, and includes, for example, aromatic hydrocarbons such as benzene, toluene, xylene; ethers such as dioxane, dimethoxyethane, tetrahydrofuran; amides such as N,N-dimethylformamide, and it is preferably tetrahydrofuran or N,N-dimethylformamide.

The usable palladium catalyst includes, for example, a palladium catalyst such as dichlorobis(triphenylphosphine)palladium(II), tetrakis(triphenylphosphine)palladium(0), tris(dibenzylideneacetone)dipalladium(0), bis(dibenzylideneacetone)palladium(0), bis(tri-t-butylphosphine)palladium(0), palladium black, etc., and preferably dichlorobis(triphenylphosphine)palladium(II) or tetrakis(triphenylphosphine)palladium(0).

The usable base includes, for example, bases such as potassium t-butoxide, sodium t-butoxide, cesium carbonate, and preferably cesium carbonate.

Although the reaction temperature may vary depending on starting materials, solvent, palladium catalysts, etc., it is typically 50 to 200° C., and preferably 70 to 150° C.

Although the reaction time may vary depending on starting materials, solvent, palladium catalyst, reaction temperature, etc., it is typically 30 minutes to 48 hours, and preferably 5 to 12 hours.

(2) In the case that $R^{2a}$ is vinyl or allyl group

This step is a step where Compound (7) and tributyl (vinyl) tin or allyltributyltin are made to react in the presence of a palladium catalyst in the absence of a solvent or in an inert solvent to produce Compound (8).

The usable solvent is not particularly limited as long as it can dissolve the starting materials to some extent and does not inhibit the reaction, and includes, for example, aromatic hydrocarbons such as benzene, toluene, xylene; ethers such as dioxane, dimethoxyethane, tetrahydrofuran; amides such as N,N-dimethylformamide, and it is preferably tetrahydrofuran or N,N-dimethylformamide.

The usable palladium catalyst includes, for example, a palladium catalyst such as dichlorobis(triphenylphosphine) palladium(II), tetrakis(triphenylphosphine)palladium(0), tris (dibenzylideneacetone)dipalladium(0), bis(dibenzylideneacetone)palladium(0), bis(tri-t-butylphosphine)palladium(0), palladium black, etc., and preferably dichlorobis(triphenylphosphine)palladium(II) or tetrakis(triphenylphosphine) palladium(0).

Although the reaction temperature may vary depending on starting materials, solvent, palladium catalysts, etc., it is typically 50 to 200° C., and preferably 70 to 150° C.

Although the reaction time may vary depending on starting materials, solvent, palladium catalyst, reaction temperature, etc., it is typically 30 minutes to 48 hours, and is preferably 5 to 12 hours.

(Step B-5) Reduction Reaction

This step is a step where hydrogen is made to react with Compound (8) in the absence of a solvent or in an inert solvent, in the presence of a reduction catalyst, or a reducing agent is made to react with Compound (8) in the absence of a solvent or in an inert solvent, and a nitro group and an alkenyl group is converted into an amino group and an alkyl group.

Also included in this step is a step where when $R^1$ is a C2-C6 alkynyl group, only a nitro group is reduced without reducing the triple bond.

The usable solvent is not particularly limited as long as it can dissolve the starting materials to some extent and does not inhibit the reaction, and includes, for example, alcohols such as methanol, ethanol, n-propanol, isopropanol, n-butanol, isobutanol, t-butanol, isoamyl alcohol, diethylene glycol, glycerin, octanol, cyclohexanol, methyl cellosolve; ethers such as diethyl ether, diisopropyl ether, tetrahydrofuran, dioxane, dimethoxyethane, diethylene glycol dimethyl ether; aliphatic hydrocarbons such as hexane, heptane, ligroin, petroleum ether; organic acid esters such as ethyl acetate, and preferably ethers, aliphatic hydrocarbons, alcohols, organic acid ester, or a mixture of these, and most preferably methanol or tetrahydrofuran.

The usable catalyst includes, for example, palladium-carbon, Raney nickel, nickel (II) chloride, platinum oxide, platinum black, rhodium-aluminum oxide, triphenylphosphine-rhodium chloride, palladium-barium sulfate, etc., and preferably palladium/carbon or nickel (II) chloride. When progress of the reaction is slow, a reduction catalyst can also be used in an amount of the weight ratio to the materials of about 1/2.

Although the reaction temperature in the case of using a reduction catalyst may vary depending on starting materials and solvents, it is typically 0 to 60° C., and preferably 10 to 40° C.

Although the reaction time in the case of using a reduction catalyst may vary depending on starting materials, solvent, and reaction temperature, it is typically 1 to 60 hours and preferably 5 to 24 hours.

Typically, the hydrogen pressure at the time of the reaction in the case of using a reduction catalyst is 0.5 to 5 atm, and preferably 1 to 2 atm.

In the case where an alkenyl group is reduced simultaneously with a nitro group, nickel (II) chloride is used as a catalyst and the reaction can be performed with sodium borohydride, etc., at −30 to 40° C. (preferably −15 to 25° C.) for 30 minutes to 1 hour.

In addition, when $R^1$ is a C2-C6 alkynyl group, and in the case that only the nitro group is reduced without reducing the triple bond, the reaction can be performed using iron-hydrochloric acid, zinc-acetic acid, iron-ammonium chloride, etc., at 0 to 30° C. for 10 to 50 hours.

Typically, the compound obtained at the B-5 step can be used in the following B-6 step by merely filtering the catalyst off.

(Step B-6) Cyclization Reaction

This step is a step where carbon bisulfide is made to react with the compound obtained at the above described B-5 step in the absence of a solvent or in an inert solvent to produce Compound (2) which is an intermediate in the above described Process A.

The usable solvent is not particularly limited as long as it can dissolve the starting materials to some extent and does not inhibit the reaction, and includes, for example alcohols such as methanol, ethanol, n-propanol, isopropanol, n-butanol, isobutanol, t-butanol, isoamyl alcohol, diethylene glycol, glycerin, octanol, cyclohexanol, methyl cellosolve; aliphatic hydrocarbons such as hexane, heptane, ligroin, petroleum ether; aromatic hydrocarbons such as benzene, toluene, ethers such as dioxane, dimethoxyethane, diethylene glycol dimethyl ether; halogenated hydrocarbons such as chloroform, dichloromethane, 1,2-dichloroethane, carbon tetrachloride; amides such as formamide, N,N-dimethylformamide, N,N-dimethylacetamide, hexamethylphosphoric triamide; organic acid such as acetic acid, etc., preferably an alcohol and most preferably methanol or N,N-dimethylformamide.

Although the reaction temperature may vary depending on starting materials and solvent, it is typically 0 to 60° C., and preferably 10 to 40° C.

Although the reaction time may vary depending on starting materials, solvent, and reaction temperature, it is typically 12 to 60 hours and preferably 24 to 48 hours.

(Step B-7)

This step is a step where ammonia is made to react with Compound (4a) in the presence or absence of alkaline metal carbonate in the absence of a solvent or in an inert solvent to produce Compound (6). This step can be performed according to the B-1 step.

As Compound (4a), a commercially available compound or a compound synthesized based on a process known by publication can be used.

Compound (2a) in which $R^2$ of Compound (2) is methyl group can be produced by the following Process C.

Process C

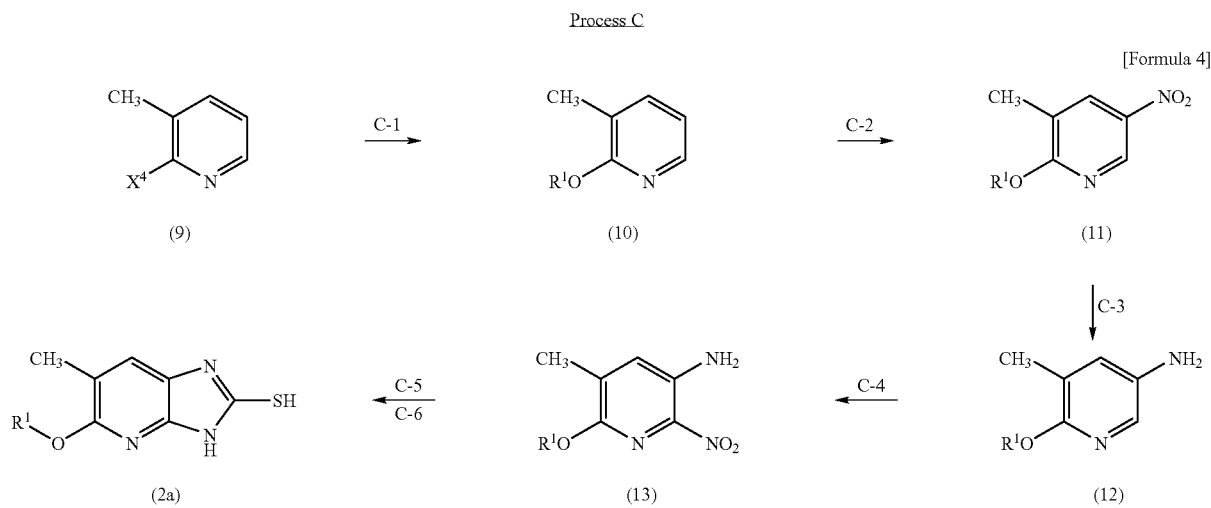

[Formula 4]

In the above scheme, $R^1$ is as defined above, $X^4$ represents a leaving group, preferably a fluorine atom, a chlorine atom, a bromine atom, or an iodine atom, and more preferably a fluoride atom.

(Step C-1) $R^1$—O group introducing reaction

This step is a step where Compound (9), and an alcohol or phenol $R^1$—OH (wherein $R^1$ is as defined above) is made to react with produce Compound (10).

As Compound (9), a commercially available compound or a compound synthesized based on a process known by publication can be used.

This process can be performed according to the above described B-2 step.

(Step C-2) Nitration Reaction

This step is a step where fuming nitric acid is made to react with Compound (10) in the presence or absence of concentrated sulfuric acid, in the absence of a solvent to produce Compound (11).

Although the reaction temperature may vary depending on starting materials and solvent, it is typically −20 to 100° C., and more preferably 0 to 80° C.

Although the reaction time may vary depending on starting materials, solvent, and reaction temperature, it is typically 6 to 48 hours and preferably 7 to 36 hours.

(Step C-3) Reduction Reaction

This step is a step where hydrogen is made to react with Compound (11) in the presence of a reduction catalyst in the absence of a solvent or in an inert solvent to produce Compound (12). This process can be performed according to the above described step B-5.

(Step C-4) Nitro Group Introduction Reaction

This step is a step where Compound (12) is made to react in an anhydrous acetic acid at 0 to 40° C. for 1 to 10 hours to obtain a compound converted into N-acetyl form (Step C-4-1), subsequently fuming nitric acid is made to react with Compound (12) in the presence or the absence of concentrated sulfuric acid, in the absence of a solvent at 0 to 40° C. for 1 to 10 hours to obtain Compound (13) (Step C-4-2), and further, the compound obtained at the preceding step is made to react with an alkaline metal hydroxide such as sodium hydroxide in an alcohol such as methanol and ethanol or a mixture of the alcohol and water at 0 to 40° C. for 5 to 30 minutes to produce Compound (13).

(Step C-5) Reduction Reaction

This step is a step where hydrogen gas is made to react with Compound (13) in the presence of a reduction catalyst in the absence of a solvent or in an inert solvent, to convert a nitro group into an amino group. This process can be performed according to the above described step B-5.

(Step C-6) Cyclization Reaction

This step is a step where carbon bisulfide is made to react with the compound obtained at the above described step C-5 in the absence of a solvent or in an inert solvent to produce Compound (2a) in which $R^2$ is methyl group among the intermediates of the above described Process A. This process can be performed according to the above described step B-6.

Compound (3a) in which $R^3$ of Compound (3) is ethyl group can be produced by the following Process D.

Process D

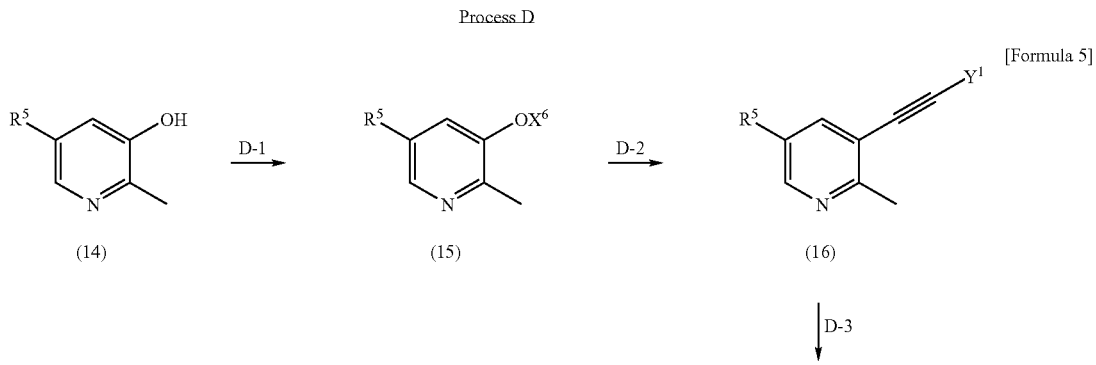

[Formula 5]

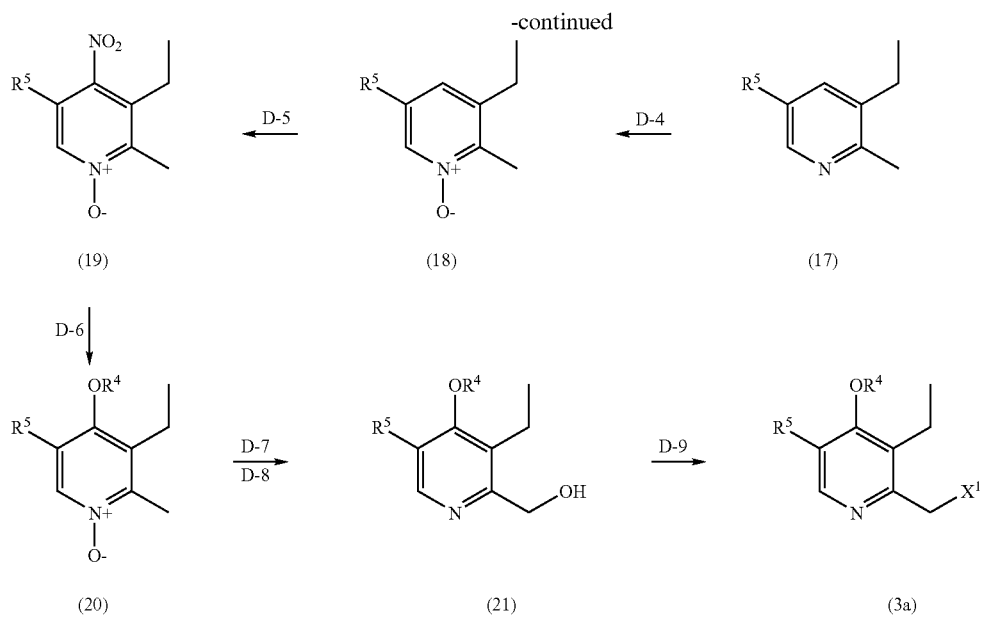

In the above scheme, $R^4$, $R^5$ and $X^1$ represent the same as defined above, $Y^1$ represents a trialkylsilyl group, preferably trimethylsilyl group and $X^6$ represents an alkylsulfonyl group which may be substituted with a halogen atom or a benzene sulfonyl group which may be substituted (for example, with trifluoromethanesulfonyl, methanesulfonyl, ethanesulfonyl, benzenesulfonyl, p-toluenesulfonyl group, etc.).

(Step D-1) Leaving Group Introduction Reaction

This step is a step where Compound (14) and a leaving group introduction agent are made to react in the presence of a base in the absence of a solvent or in an inert solvent to produce Compound (15).

As Compound (14), a commercially available compound or a compound synthesized based on a process known by publication can be used.

The usable solvent is not particularly limited as long as it can dissolve the starting materials to some extent and does not inhibit the reaction, and includes, for example, halogenated hydrocarbons such as chloroform, dichloromethane, 1,2-dichloroethane, carbon tetrachloride; aromatic hydrocarbon such as benzene, toluene; ethers such as diethyl ether, diisopropyl ether, tetrahydrofuran, dioxane, dimethoxyethane, diethylene glycol dimethyl ether; amides such as formamide, N,N-dimethylformamide, N,N-dimethylacetamide, hexamethylphosphoric triamide, pyridine, etc., and preferably a halogenated hydrocarbon and most preferably dichloromethane.

The usable leaving group introduction agent includes, for example, sulfonyl halides such as methanesulfonylchloride, p-toluenesulfonylchloride, trifluoromethanesulfonylchloride, N-phenyl-bis(trifluoromethanesulfonimide), and preferably N-phenyl-bis(trifluoromethanesulfonimide).

The usable base includes, for example, tertiary alkylamines such as trimethylamine and triethylamine, pyridines, etc., and it is preferably triethylamine.

Although the reaction temperature may vary depending on starting materials, solvent, leaving group introduction agent and bases, it is typically 0 to 100° C., and preferably 0 to 40° C.

Although the reaction time may vary depending on starting materials, solvent, leaving group introduction agent, base, and reaction temperature, it is typically 6 to 48 hours and preferably 12 to 30 hours.

(Step D-2) Alkyne Introduction Reaction

This step is a step where Compound (15) and (trialkylsilyl)acetylene are made to react in the presence of a palladium catalyst, a copper catalyst and a base in the absence of a solvent or in an inert solvent, and under nitrogen atmosphere to produce Compound (16).

The usable solvent is not particularly limited as long as it can dissolve the starting materials to some extent and does not inhibit the reaction, and includes, for example, ethers such as diethyl ether, tetrahydrofuran, dioxane, dimethoxyethane, diethylene glycol dimethyl ether; amides such as formamide, N,N-dimethylformamide, N,N-dimethylacetamide, hexamethylphosphoric triamide, pyridine, etc., and preferably an amide and most preferably N,N-dimethylformamide.

The usable palladium catalyst includes, for example, dichlorobis(triphenylphosphine)palladium(0), tetrakis(triphenylphosphine)palladium(0), tris (dibenzylideneacetone)dipalladium(0), bis(dibenzylideneacetone)palladium(0), bis (tri-t-butylphosphine)palladium(0), palladium black, etc., and preferably dichlorobis (triphenylphosphine)palladium (0).

The usable copper catalyst includes, for example, copper (powder), copper(I) chloride, copper(II) chloride, copper(I) iodide, copper(I) oxide, copper(II) oxide, copper(II) acetate, copper(II) sulfate pentahydrate, copper(II) acetylacetonate, copper(I) thiocyanate, etc., and preferably copper(I) iodide.

The usable base includes, for example, N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino) pyridine, 2,6-di(t-butyl)-4-methylpyridine, quinoline, N,N-dimethyl aniline, N,N-diethyl aniline, 1,5-diazabicyclo[4.3.0]nona-5-ene (DBN), 1,4-diazabicyclo[2.2.2]octane (DABCO), 1,8-diazabicyclo[5.4.0]undeca-7-ene (DBU) etc., and it is preferably triethylamine.

The usable (trialkylsilyl)acetylene includes, for example, (trimethylsilyl)acetylene, (triethylsilyl)acetylene, etc., and it is preferably (trimethylsilyl)acetylene.

Although the reaction temperature may vary depending on starting materials, solvent, a palladium catalyst, copper catalyst, base and (trialkylsilyl)acetylene, it is typically 10 to 100° C., and preferably 30 to 80° C.

Although the reaction time may vary depending on starting materials, solvent, palladium catalyst, copper catalyst, base, (trialkylsilyl)acetylene and reaction temperature, it is typically 10 minutes to 4 hours, and preferably 30 minutes to 3 hours.

(Step D-3) Desilylation Reaction, Reduction Reaction

This process consists of the following 2 reaction steps.

(1) Desilylation Reaction

This step is a step where a desilylating agent was made to react to Compound (16) in the absence of a solvent or in an inert solvent to produce a desilylated compound.

The usable solvent is not particularly limited as long as it can dissolve the starting materials to some extent and does not inhibit the reaction, and includes, for example, alcohols such as methanol, ethanol, n-propanol, isopropanol, n-butanol, isobutanol, t-butanol, isoamyl alcohol, diethylene glycol, glycerin, octanol, cyclohexanol and methyl cellosolve; aliphatic hydrocarbons such as hexane, heptane, ligroin, petroleum ether; halogenated hydrocarbons such as chloroform, dichloromethane, 1,2-dichloroethane and carbon tetrachloride; ethers such as diethyl ether, diisopropyl ether, tetrahydrofuran, dioxane, dimethoxyethane, diethylene glycol dimethyl ether; amides such as formamide, N,N-dimethylformamide, N,N-dimethylacetamide, hexamethylphosphoric triamide, and it is preferably an ether and most preferably tetrahydrofuran.

The usable desilylating agent includes, for example, hydrogen fluoride, tetrabutylammonium fluoride, etc., and it is preferably tetrabutylammonium fluoride.

Although the reaction temperature may vary depending on starting materials, solvent, and desilylating agent, it is typically 0 to 100° C., and preferably 10 to 40° C.

Although the reaction time may vary depending on starting materials, solvent, and desilylating agent, it is typically 30 minutes to 6 hours, and preferably 2 to 3 hours.

Since the compound obtained in this step may be a low boiling point compound, and in that case, the solution is typically used for the subsequent process without any treatment of concentration after reaction, extraction, column chromatography, etc.

(2) Reduction Reaction

This step is a step where hydrogen gas is made to react with the compound obtained at the above described step (1) in the presence of a reduction catalyst in an inert solvent to produce Compound (17).

This process can be performed according to the above described step B-2. However, the reduction catalyst is typically used in a weight ratio of about 5-10% to the compound obtained at the above described step (1).

(Step D-4) Oxidation Reaction

This step is a step where an oxidizing reagent is made to react with Compound (17) in the absence of a solvent or in an inert solvent to produce Compound (18).

The usable solvent is not particularly limited as long as it can dissolve the starting materials to some extent and does not inhibit the reaction, and includes, for example, aliphatic hydrocarbons such as hexane, heptane, ligroin, petroleum ether; halogenated hydrocarbons such as chloroform, dichloromethane, 1,2-dichloroethane, carbon tetrachloride; ethers such as diethyl ether, diisopropyl ether, tetrahydrofuran, dioxane, dimethoxyethane, diethylene glycol dimethyl ether; amides such as formamide, N,N-dimethylformamide, N,N-dimethylacetamide, hexamethylphosphoric triamide; organic acids such as acetic acid, etc., and it is preferably an organic acid and most preferably acetic acid.

The usable oxidizing reagent includes, for example, hydrogen peroxide, t-butyl hydroperoxide, sodium periodate, peracetic acid, perbenzoic acid, metachloroperbenzoic acid, urea-hydrogen peroxide addition compound, etc., and it is preferably hydrogen peroxide or urea-hydrogen peroxide addition compound. In addition, when using urea-hydrogen peroxide addition compound, it is usually desirable to use the compound along with anhydrous trifluoroacetic acid and the like.

Although the reaction temperature may vary depending on starting materials, solvent, and oxidizing reagent, it is typically 30 to 150° C., and preferably 50 to 100° C.

Although the reaction time may vary depending on starting materials, solvent, oxidizing reagent and reaction temperature, it is typically 12 to 60 hours and preferably 24 to 36 hours.

(Step D-5) Nitration Reaction

This step is a step where fuming nitric acid is made to react with Compound (18) in the absence or presence of concentrated sulfuric acid in the absence of a solvent or in an inert solvent to produce Compound (19).

This step can be performed according to the above described step C-2.

(Step D-6) $R^4$—O Forming Reaction

This step is a step where an alcoholic $R^4$—OH (wherein $R^4$ is as defined above) is made to react with Compound (19) in the presence of a base in the absence of a solvent or in an inert solvent to produce Compound (20).

The usable solvent is not particularly limited as long as it can dissolve the starting materials to some extent and does not inhibit the reaction, and includes, for example, alcohols such as methanol, ethanol, n-propanol, isopropanol, n-butanol, isobutanol, t-butanol, isoamyl alcohol, diethylene glycol, glycerin, octanol, cyclohexanol and methyl cellosolve; aliphatic hydrocarbons such as hexane, heptane, ligroin, petroleum ether; halogenated hydrocarbons such as chloroform, dichloromethane, 1,2-dichloroethane and carbon tetrachloride; ethers such as diethyl ether, diisopropyl ether, tetrahydrofuran, dioxane, dimethoxyethane, diethylene glycol dimethyl ether; amides such as formamide, N,N-dimethylformamide, N,N-dimethylacetamide and hexamethylphosphoric triamide; organic acid such as acetic acid, etc., and it is preferably an alcohol ($R^4$—OH).

The usable base includes, for example, alkaline metal alkoxide such as sodium methoxide and sodium ethoxide, and it is preferably sodium alkoxide (desired $R^4$—ONa).

Although the reaction temperature may vary depending on starting materials, solvent and base, it is typically 0 to 100° C., and preferably 10 to 60° C.

Although the reaction time may vary depending on the starting materials, solvent, base and reaction temperature, it is typically 5 to 24 hours and preferably 8 to 14 hours.

(Step D-7) Acetic Acid Esterification Reaction

This step is a step where anhydrous acetic acid is made to react with Compound (20) in the absence of a solvent to produce an acetic acid ester of Compound (21).

Although the reaction temperature may vary depending on starting materials and solvent, it is typically 20 to 150° C., and preferably 50 to 100° C.

Although the reaction time may vary depending on starting materials, solvent and reaction temperature, it is typically 10 minutes to 3 hours, and preferably 1 to 2 hours.

The residue after the reaction obtained by evaporating anhydrous acetic acid is typically used for the subsequent step without any treatment.

(Step D-8) Hydrolysis Reaction

This step is a step where a base is made to react with the compound obtained at the above described step D-7 process in the absence of a solvent or in an inert solvent to produce Compound (21).

The usable solvent is not particularly limited as long as it can dissolve the starting materials to some extent and does not inhibit the reaction, and includes, for example, water; alcohols such as methanol, ethanol, n-propanol, isopropanol, n-butanol, isobutanol, t-butanol, isoamyl alcohol, diethylene glycol, glycerin, octanol, cyclohexanol and methyl cellosolve; aliphatic hydrocarbons such as hexane, heptane, ligroin, petroleum ether; ethers such as dioxane, dimethoxyethane, diethylene glycol dimethyl ether; halogenated hydrocarbons such as chloroform, dichloromethane, 1,2-dichloroethane and carbon tetrachloride; ethers such as diethyl ether, diisopropyl ether, tetrahydrofuran, dioxane, dimethoxyethane, diethylene glycol dimethyl ether; amides such as formamide, N,N-dimethylformamide, N,N-dimethylacetamide, hexamethylphosphoric triamide, and it is preferably an alcohol or a mixture of alcohol and water, and most preferably a mixture of methanol and water.

The usable base includes, for example, alkaline metal carbonates such as lithium carbonate, sodium carbonate, potassium carbonate; alkaline metal hydroxide such as lithium hydroxide, sodium hydroxide, potassium hydroxide; metal alkoxide such as lithium methoxide, sodium methoxide, sodium ethoxide, potassium t-butoxide; ammonia such as aqueous ammonia solution, concentrated ammonia-methanol, etc., and it is preferably an alkaline metal hydroxide and most preferably sodium hydroxide.

Although the reaction temperature may vary depending on starting materials, solvent and base, it is typically 0 to 60° C., and preferably 10 to 40° C.

Although the reaction time may vary depending on the starting materials, solvent, base and reaction temperature, it is typically 10 minutes to 2 hours, and preferably 30 minutes to 1 hour.

(Step D-9)

(1) Halogenation Reaction (Illustrated by Chlorination Reaction as a Representative Reaction)

This step is a step where a chlorinating agent is made to react with Compound (21) in the absence of a solvent or in an inert solvent to produce Compound (3a) in which $R^3$ is an ethyl group among the intermediates of the above described Process A.

The usable solvent is not particularly limited as long as it can dissolve the starting materials to some extent and does not inhibit the reaction, and includes, for example, halogenated hydrocarbons such as chloroform, dichloromethane, 1,2-dichloroethane, carbon tetrachloride, and it is preferably a halogenated hydrocarbon and most preferably dichloromethane.

The usable chlorinating agent includes, for example, chlorine, oxalyl chloride, thionyl chloride, phosphorus oxychloride, phosphorus trichloride, phosphorus pentachloride, etc., and it is preferably thionyl chloride.

Although the reaction temperature may vary depending on starting materials, solvent and chlorinating agents, it is typically −20 to 30° C., and preferably 0 to 10° C.

Although the reaction time may vary depending on starting materials, solvent, chlorinating agent and reaction temperature, it is typically 30 minutes to 6 hours, and preferably 1 to 2 hours.

Compound (3a) of this step can be obtained as a hydrochloride salt, and can also be used without any treatment.

(2) Leaving Group Introduction Reaction

This step is a step where Compound (21) and a leaving group introduction agent are made to react in the presence of base in the absence of a solvent or in an inert solvent to produce Compound (3a) in which $R^2$ is methyl group. This step can be performed such as the above described step D-1.

Compound (2b) in which $R^2$ of Compound (2) is methyl group can be also produced by the following Process E.

Process E

[Formula 6]

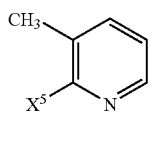 →E-1→ 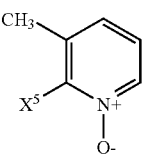 →E-2→ 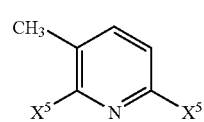

(22)　　　　　　　　(23)　　　　　　　　(24)

↓E-3

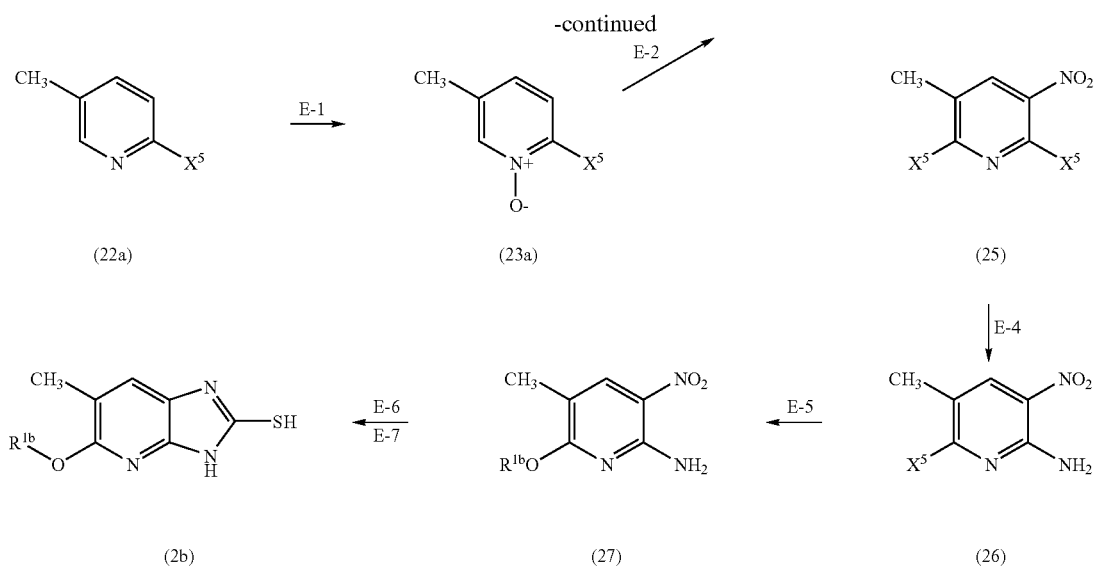

In the above scheme, $R^{1b}$ is as defined above, and $X^5$ represents a leaving group and is a chlorine atom, a bromine atom or an iodine atom, and preferably a chlorine atom.

(Step E-1) Oxidation Reaction

This step is a step where an oxidizing reagent is made to react with Compound (22) or Compound (22a) in the absence of a solvent or in an inert solvent to produce Compound (23) or Compound (23a).

As Compounds (22) and (22a), commercially available compounds or compounds synthesized according to any process known by publication can be used.

This step can be performed according to the above described step D-4.

(Step E-2) Leaving Group Introduction Reaction (Illustrated by Chlorination Reaction as a Representative Reaction)

This step is a step where a chlorinating agent is made to react with Compound (23) or Compound (23a) in the presence of a base in the absence of a solvent or in an inert solvent to produce Compound (24).

The usable solvent is not particularly limited as long as it can dissolve the starting materials to some extent and does not inhibit the reaction, and includes, for example, halogenated hydrocarbons such as chloroform, dichloromethane, 1,2-dichloroethane, carbon tetrachloride, and it is preferably a halogenated hydrocarbon and most preferably dichloromethane.

The usable base includes, for example, N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino) pyridine, 2,6-di(t-butyl)-4-methylpyridine, quinoline, N,N-dimethyl aniline, N,N-diethyl aniline, 1,5-diazabicyclo[4.3.0]nona-5-ene (DBN), 1,4-diazabicyclo[2.2.2]octane (DABCO), 1,8-diazabicyclo[5.4.0]undeca-7-ene (DBU), etc., and it is preferably triethylamine.

The usable chlorinating agent includes, for example, chlorine, oxalyl chloride, thionyl chloride, phosphorus oxychloride, phosphorus trichloride, phosphorus pentachloride, etc., and it is preferably thionyl chloride.

Although the reaction temperature may vary depending on starting materials, solvent and chlorinating agents, it is typically −20 to 30° C., and preferably 0 to 10° C.

Although the reaction time may vary depending on starting materials, solvent, chlorinating agent and reaction temperature, it is typically 30 minutes to 6 hours, and preferably 1 to 2 hours.

(Step E-3) Nitration Reaction

This step is a step where fuming nitric acid is made to react with Compound (24) in the absence or presence of concentrated sulfuric acid in the absence of a solvent to produce Compound (25).

This process can be performed according to the above described step C-2.

(Step E-4) Amination Reaction

This step is a step where aqueous ammonia solution is made to react with Compound (25) in the presence of alkaline metal carbonate in the absence of a solvent or in an inert solvent to produce Compound (26). This step can be performed according to the above described step B-1.

(Step E-5) $R^1$—O-Group Introduction Reaction

This step is a step where Compound (26) and an alcohol or phenol $R^1$—OH (wherein $R^1$ is as defined above) is made to react, to produce Compound (27).

This step can be performed according to the above described step B-2.

(Step E-6) Reduction Reaction

This step is a step where hydrogen is made to react with Compound (27) in the presence of a reduction catalyst in the absence of a solvent or in an inert solvent, and a nitro group is converted to an amino group. This step can be performed according to the above described step B-5.

(Step E-7) Cyclization Reaction

This step is a step where carbon bisulfide is made to react with the compound obtained at the above described step B-5 in the absence of a solvent or in an inert solvent to produce Compound (2b) in which $R^2$ is methyl group among the intermediates of the above described Process A. This step can be performed according to the above described step B-6.

The object compound of each step can be extracted from the reaction mixture according to ordinary process after each step of each of the above processes is ended.

For example, when the whole reaction mixture is a liquid, the reaction mixture is optionally allowed to be cooled to room temperature or ice-cooled, and the acid, alkali, oxidizing reagent, or reducing agent is suitably neutralized, and an organic solvent which is immiscible like water and ethyl acetate and does not react with the object compound is added, and the layer containing the object compound is separated. Next, a solvent which does not mix with the obtained layer and does not react with the object compound is added, the layer containing the object compound is washed, and the layer concerned is separated. In addition, if the layer concerned is an organic layer, it can be dried using a drying agent such as anhydrous magnesium sulfate or anhydrous sodium sulfate, and the object compound can be taken out by evaporating the solvent. If the layer concerned is an aqueous layer, after it is electrically desalted, the object compound can be obtained by freeze-drying.

In addition, in the case that the whole reaction mixture is a liquid, and if possible, the object compound can be taken out only by evaporating substances other than the object compound (for example, solvent, reagents, etc.) under ordinary or reduced pressure.

Furthermore, when only the object compound has precipitated as a solid, or when the above described whole reaction mixture is a liquid and only the object compound has precipitated as a solid in process of obtaining the compound, first, the object compound is taken out by filtering method and the obtained object compound is washed with a suitable organic or inorganic solvent, and then dried, and the mother liquid is treated just like the above described case where the whole reaction mixture is a liquid to further obtain the object compound.

Furthermore, when only a reagent or catalyst exists as a solid, or when the above described whole reaction mixture is a liquid and only a reagent or catalyst precipitates as a solid in process of extraction and the object compound is dissolving in the solution, the reagent or catalyst is first filtered off by the filtering method, and the object compound is washed with a suitable organic or inorganic solvent, and the resulting washing liquid is combined with the mother liquid, and the resulting mixed solution is treated just like the above described case where the whole reaction mixture is a liquid to obtain the object compound.

Especially when those contained in the reaction mixture other than the object compound do not inhibit the reaction of the subsequent step, the reaction mixture can also be used without any treatment for the subsequent step without particularly isolating the object compound.

For the purpose of improving the purity of the object compound extracted by the above described method, recrystallization method, various chromatography methods, and distillation method can be suitably performed.

When the extracted object compound is a solid, the purity of the object compound can typically be improved by recrystallization method. In the recrystallization method, a single solvent or two or more mixtures which do not react with the object compound can be used. Specifically, the object compound is first dissolved in a single or multiple solvents which do not react with the object compound at room temperature or under heating. The resulting mixed solution is cooled with iced water or allowed to leave at room temperature, and the object compound is allowed to recrystallize from the mixed solution.

When the extracted object compound is a liquid, the purity of the object compound can be improved by various chromatography methods. Generally, weak acidic silica gels such as Silica Gel 60 produced by Merck Co. (70-230 mesh or 340-400 mesh) or BW-300 produced by Fuji Silysia Chemical Co., Ltd. (300 mesh) can be used. When the object compound has basic properties, and the above described silica gels are excessively adsorptive, propylamine coating silica gel (200-350 mesh) by Fuji Silysia Chemical Co., Ltd. etc., can also be used. When the object compound has bipolarity, or when it is required to be eluted with a high polarity solvent such as methanol, NAM-200H or NAM-300H produced by NAMU Research Institute can also be used. The object compound whose purity is improved can be obtained by using these silica gels and eluting the object compound with a single or multiple solvents which do not react with the object compound, and evaporating the solvent.

When the extracted object compound is a liquid, the purity of the object compound can be improved also by distillation method. The object compound can be distilled under reduced pressure at room temperature or under heating in the distillation method.

The above is to illustrate representative examples of the process for producing Compound (1) of the present invention, and the material compounds and the various reagents in the production of the present invention may form a salt, hydrate or solvate, and each of them may vary depending on starting materials, solvents to be used, etc., and are not particularly limited unless they do not inhibit the reaction. The usable solvents may vary depending on starting materials, reagents, etc., and needless to say, they are not particularly limited as long as they can dissolve the starting materials to some extent and do not inhibit the reaction. When Compound (1) concerning the present invention is obtained as a free form, it can be converted to the state of a salt or hydrate thereof which the above described Compound (1) may form according to an ordinary process.

When Compound (1) of the present invention is obtained as a salt or hydrate of Compound (1), it can converted to a free form of the above described Compound (1) according to an ordinary process.

Moreover, various isomers (for example, geometric isomer, optical isomer, rotational isomer, stereoisomer, tautomer, etc.) obtainable for Compound (1) of the present invention can be purified and isolated by using usual separation means, for example, recrystallization, diastereomer salt method, enzymatic dividing method, and various chromatography (for example, thin layer chromatography, column chromatography, gas chromatography, etc.).

When the compound of the present invention is used as drug, typically, suitable additive agents are mixed with the compound of the present invention to form preparation. However, this does not deny the use of the compound of the present invention without any treatment as a drug.

As the above described additive agent generally used for drugs, excipient, binder, lubricant, disintegrating agent, colorant, flavor, emulsifier, surfactant, dissolution auxiliary agent, suspending agent, isotonizing agent, buffering agent, antiseptic, anti-oxidizing agent, stabilizing agent, absorption improver, etc. can be mentioned, and these can also be optionally used in a suitable combination.

Examples of the above described excipient include lactose, sucrose, glucose, cornstarch, mannitol, sorbitol, starch, gelatinized starch, dextrin, crystalline cellulose, light anhydrous silicic acid, aluminum silicate, calcium silicate, magnesium aluminometasilicate, calcium hydrogen phosphate, etc.

Examples of the above described binder include polyvinyl alcohol, methyl cellulose, ethyl cellulose, gum arabic, gum tragacanth, gelatin, shellac, hydroxypropyl methylcellulose, hydroxypropyl cellulose, carboxymethylcellulose sodium, polyvinylpyrrolidone, macrogol, etc.

Examples of the above described lubricant include magnesium stearate, calcium stearate, sodium stearyl fumarate, talc, polyethylene glycol, colloidal silica, etc.

Examples of the above described disintegrating agent include crystal cellulose, agar, gelatin, calcium carbonate, sodium bicarbonate, calcium citrate, dextrin, pectin, low substituted hydroxypropylcellulose, carboxymethyl cellulose, carboxymethyl cellulose calcium, croscarmellose sodium, carboxymethyl starch, carboxymethyl starch sodium, etc.

Examples of the above described colorant include those permitted to add to drugs such as iron sesquioxide, yellow iron sesquioxide, carmine, caramel, beta-carotene, titanium oxide, talc, riboflavin sodium phosphate, and yellow aluminum lake.

Examples of the above described flavor include cocoa powder, peppermint, aromatic powder, peppermint oil, camphol, cinnamon powder, etc.

Examples of the above described emulsifier or surfactant include stearyltriethanolamine, sodium lauryl sulfate, lauryl aminopropionate, lecithin, glyceryl monostearate, sucrose fatty acid ester, glycerin fatty acid ester, etc.

Examples of the above described dissolution auxiliary agent include polyethylene glycol, propylene glycol, benzoic acid benzyl ester, ethanol, cholesterol, triethanolamine, sodium carbonate, sodium citrate, Polysorbate 80, nicotinamide, etc.

Examples of the above described suspending agent include, besides the above described surfactant, hydrophilic polymers such as polyvinyl alcohol, polyvinylpyrrolidone, methyl cellulose, hydroxymethyl cellulose, hydroxyethyl cellulose, hydroxypropyl cellulose.

Examples of the above described isotonizing agent include glucose, sodium chloride, mannitol, sorbitol, etc.

Examples of the above described buffering agent include buffer solution such as phosphate, acetate, carbonate, citrate, etc.

Examples of the above described antiseptic include methylparaben, propyl paraben, chlorobutanol, benzyl alcohol, phenethyl alcohol, dehydroacetic acid, sorbic acid, etc.

Examples of the above described anti-oxidizing agent include sulfurous acid salt, ascorbic acid, alpha-tocopherol, etc.

Examples of the above described stabilizing agent include those generally used for drugs.

Examples of the above described absorption improver include those generally used for drugs.

Examples of the above described preparation include oral agent such as tablet, powder drug, granule agent, capsule agent, syrup agent, troche agent, and inhalation agent; external preparations such as suppository, ointment, eye ointment, tapes, eye drop, nose drop, ear drop, pap agent, lotion or an injection agent.

The above described oral agent is prepared by suitably combining the above described additives. The surface of it may be coated if needed.

The above described external preparations is prepared by suitably combining the above described additives, particularly excipient, binder, flavor, emulsifier, surfactant, dissolution auxiliary agent, suspending agent, isotonizing agent, antiseptic, anti-oxidizing agent, stabilizing agent or absorption improver.

The above described injection agent prepared by suitably combining the above described additives, particularly emulsifier, surfactant, dissolution auxiliary agent, suspending agent, isotonizing agent, buffering agent, antiseptic, anti-oxidizing agent, stabilization agent or absorption improver.

When using the compound of the present invention as drug, the dosage varies depending on condition or age, and typically, 0.15 to 5000 mg (preferably 0.5 to 1500 mg) in the case of oral agent, 0.5 to 1500 mg (preferably 1.5 to 500 mg) in the case of external preparation, 0.3 to 5000 mg (preferably 1 to 500 mg) for one time or divided to 2 to 6 times per day in the case of injection agent. The above described values are actually administered values for oral agent and injection agent and a value actually absorbed by a living body for external preparation.

Compound (1) of the present invention can be produced, for example, by the process indicated in the following Examples, and the effect of the compound can be confirmed by the method indicated for the following Test Examples. However, they are illustrative and present invention are not limited to these specific examples below in any case.

Commercially available starting materials, reagents, used in Examples and their suppliers are shown below. When the supplier is indicated by a publication name, it means that the compound was prepared according to the reference shown.

2-Fluoro-3-methylpyridine (FLUOROCHEM)
10% Pd-on-carbon powder (50% water content article) (N. E. CHEMCAT)
Carbon bisulfide (Wako Pure Chemical Industries)
2-Chloromethyl-4-methoxy-3-methylpyridine hydrochloride salt (*J. Med. Chem.*, 1992, 35, 1049-1057)
Metachloro perbenzoic acid (Tokyo Kasei Kogyo)
1N sodium hydroxide solution (Wako Pure Chemical Industries)
2-Chloro-3-methylpyridine (Aldrich)
Urea hydrogen peroxide addition compound (Aldrich)
Anhydrous trifluoroacetic acid (Tokyo Kasei Kogyo)
2-Chloro-5-methylpyridine (Aldrich)
Phosphorous oxychloride (Wako Pure Chemical Industries)
Anhydrous trifluoromethane sulfonic acid (Tokyo Kasei Kogyo)
Nitric acid tetramethyl ammonium (Aldrich)
2,2,2-trifluoro ethanol (Tokyo Kasei Kogyo)
2,2-difluoro ethanol (Lancaster)
2-Chloro-6-methoxy-3-nitropyridine (Tokyo Kasei Kogyo)
Concentrated ammonia solution (Kanto chemistry)
N-iodosuccinimide (Lancaster)
Acetic acid (Wako Pure Chemical Industries)
Trimethylboroxin (Aldrich)
Tetrakis(triphenylphosphine)palladium(0) (Kanto chemistry)

EXAMPLES

Example 1

5-Methoxy-2-(((4-methoxy-3-methyl-2-pyridinyl)methyl)sulfinyl)-6-methyl-3H-imidazo[4,5-b]pyridineSodium salt

[Formula 7]

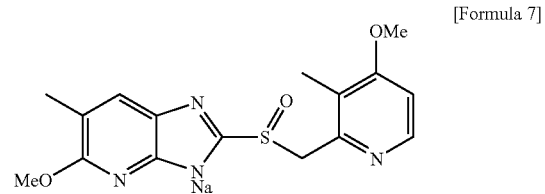

(1a) 2-Methoxy-3-methylpyridine

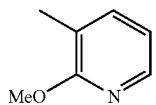

[Formula 8]

A mixture of 2-fluoro-3-methylpyridine (2.34 g, 21.1 mmol) and a 28% sodium methoxide methanol solution (7.72 g, 40 mmol) was stirred for 15 minutes under reflux. After the reaction was completed, water was poured into the reaction mixture, and after neutralized, the reaction mixture was extracted with ethyl acetate, dried over magnesium sulfate, and the solvent was evaporated, thereby yielding the title compound (1.62 g, 13.1 mmol, 62%) as a colorless liquid.

$^1$H NMR (400 MHz, DMSO-$d_6$) δ ppm; 2.13 (3H, s), 3.86 (3H, s), 6.87-6.90 (1H, m), 7.49-7.55 (1H, m), 7.96-8.02 (1H, m).

(1b) 2-Methoxy-3-methyl-5-nitropyridine

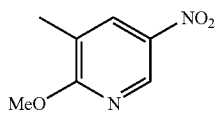

[Formula 9]

Concentrated sulfuric acid (5 ml) and fuming nitric acid (5 ml) were added to 2-methoxy-3-methylpyridine (1.61 g, 13.1 mmol) under ice cooling, and stirred at 0° C. for 1 hour and further stirred at room temperature overnight. The reaction mixture was poured onto ice, neutralized with ammonia solution, extracted with ethyl acetate, dried over magnesium sulfate, the solvent was evaporated, thereby yielding the title compound (1.63 g, 9.71 mmol, and 74%).

$^1$H NMR (400 MHz, DMSO-$d_6$) δ ppm; 2.25 (3H, s), 4.04 (3H, s), 8.37-8.40 (1H, m), 8.92-8.95 (1H, m).

(1c) 6-Methoxy-5-methyl-3-pyridinamine

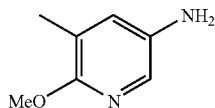

[Formula 10]

2-Methoxy-3-methyl-5-nitropyridine (1.63 g, 9.71 mmol) was dissolved in methanol (50 ml), 10% Pd-on-carbon powder (50% water content article) (800 mg) was added, and stirred under hydrogen atmosphere for 2 hours and 10 minutes. After the reaction was completed, celite filtration was carried out, the solvent was evaporated, thereby yielding the title compound (1.25 g, 0.90 mmol, 93%) as a blue oily substance.

$^1$H NMR (400 MHz, DMSO-$d_6$) δ ppm; 2.03 (3H, s), 3.73 (3H, s), 4.62 (2H, br s), 6.83-6.86 (1H, m), 7.31-7.34 (1H, m).

(1d) N-(6-methoxy-5-methyl-2-nitro-3-pyridinyl)acetamide

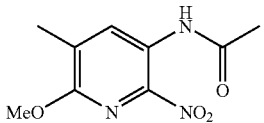

[Formula 11]

Anhydrous acetic acid (20 ml) was added to 6-methoxy-5-methyl-3-pyridineamine (1.18 g, 8.54 mmol) under ice cooling, and stirred at 0° C. for 20 minutes and at room temperature further for 1 hour. The reaction mixture was cooled at 0° C. again, fuming nitric acid (2 ml) was dropped thereto, and the mixture was stirred at 0° C. for 1 hour and 55 minutes and at room temperature further for 1 hour and 45 minutes. The reaction mixture was poured onto ice and adjusted to pH 9 with a 5N sodium hydroxide solution, extracted with ethyl acetate, and then the solvent was evaporated, thereby yielding the title compound (1.94 g) as a yellow solid crude product.

$^1$H NMR (400 MHz, DMSO-$d_6$) δ ppm; 2.05 (3H, s), 2.23 (3H, s), 3.91 (3H, s), 7.89 (1H, s), 10.10 (1H, br s).

(1e) 6-Methoxy-5-methyl-2-nitro-3-pyridinamine

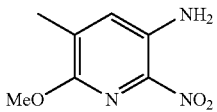

[Formula 12]

The crude product (1.93 g) of N-(6-methoxy-5-methyl-2-nitro-3-pyridinyl) acetamide was dissolved in methanol (36 ml), 5N sodium hydroxide solution (6 ml) was added, and the reaction mixture was stirred for 15 minutes at room temperature. After water was added to the reaction solution, it was extracted with ethyl acetate and dried over magnesium sulfate, and the solvent was evaporated, thereby yielding the title compound (1.06 g, 5.79 mmol) as a yellow solid.

$^1$H NMR (400 MHz, DMSO-$d_6$) δ ppm; 2.15 (3H, s), 3.84 (3H, s), 7.25 (2H, br s), 7.34 (1H, s).

(1f) 5-Methoxy-6-methyl-3H-imidazo[4,5-b]pyridine-2-thiol

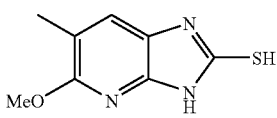

[Formula 13]

6-Methoxy-5-methyl-2-nitro-3-pyridineamine (5.40 g, 29.5 mmol) was dissolved in methanol (300 ml), 10% Pd-on-carbon powder (50% water content article) (2.73 g) was added, and the reaction mixture was stirred under hydrogen atmosphere for 5 hours and 25 minutes. After the reaction was completed, the reaction mixture was filtered, carbon bisulfide (110 ml) was added, and stirred at room temperature for 65 hours and 40 minutes under nitrogen atmosphere, and the solvent was evaporated, thereby yielding the title compound (5.59 g, 28.6 mmol, 97.1%) as a brown solid.

$^1$H NMR (400 MHz, DMSO-d$_6$) δ ppm; 2.16 (3H, s), 3.86 (3H, s), 7.35 (1H, s), 12.46 (1H, br s), 12.88 (1H, br s).

(1g) 5-Methoxy-2-(((4-methoxy-3-methyl-2-pyridinyl)methyl)thio)-6-methyl-3H-imidazo[4,5-b]pyridine

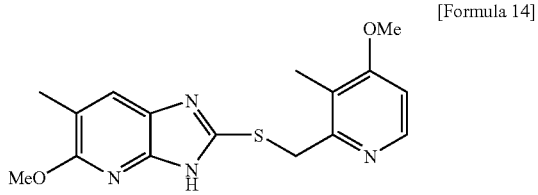

[Formula 14]

A mixture of 5-methoxy-6-methyl-3H-imidazo[4,5-b]pyridine-2-thol (971 mg, 5.0 mmol), 2-chloromethyl-4-methoxy-3-methylpyridine hydrochloride salt (1.35 g, 6.5 mmol), sodium hydroxide (822 mg) and methanol (40 ml) was stirred overnight at room temperature under nitrogen atmosphere. After the reaction was completed, the solvent was evaporated by half, ammonium chloride solution was added thereto, and the reaction mixture was extracted with chloroform (300 ml), dried over magnesium sulfate, and the solvent was evaporated, thereby yielding the crude product, which was then precipitated as a solid from a mixture of chloroform and ether, and the title compound (1.06 g, 3.22 mmol, 64%) was obtained as a purple gray solid.

$^1$H NMR (400 MHz, DMSO-d$_6$) δ ppm; 2.19 (3H, s), 2.21 (3H, s), 3.86 (3H, s), 3.90 (3H, s), 4.66 (2H, br s), 6.97 (1H, d, J=6 Hz), 7.63 (1H, br s), 8.25 (1H, d, J=6 Hz).

(1h) 5-Methoxy-2-(((4-methoxy-3-methyl-2-pyridinyl)methyl)sulfinyl)-6-methyl-3H-imidazo[4,5-b]pyridine

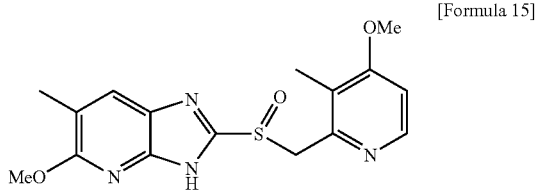

[Formula 15]

5-Methoxy-2-(((4-methoxy-3-methyl-2-pyridinyl)methyl)thio)-6-methyl-3H-imidazo[4,5-b]pyridine (784 mg, 2.37 mmol) was dissolved in a mixture of methanol (6 ml) and toluene (54 ml). Metachloroperbenzoic acid (566 mg) in a mixture solution of methanol (3 ml) and toluene (3 ml) were added thereto at −40° C. under nitrogen flow, and the reaction mixture was stirred at −20 to −40° C. for 2 hours. After the reaction was completed, a sodium bicarbonate solution was added, and the organic layer was separated. The aqueous layer was extracted with chloroform (40 ml), combined with the organic layer and dried over sodium sulfate, the solvent was evaporated and the residue was obtained which was then precipitated as a solid from a mixture of chloroform and ether, thereby yielding the title compound (654 mg, 1.89 mmol, 80%) as a purple gray solid.

$^1$H NMR (400 MHz, DMSO-d$_6$) δ ppm; 2.14 (3H, s), 2.25 (3H, s), 3.85 (3H, s), 3.94 (3H, s), 4.72 (1H, d, J=14 Hz), 4.81 (1H, br d, J=14 Hz), 6.96 (1H, d, J=6 Hz), 7.83 (1H, br s), 8.22 (1H, d, J=6 Hz).

(1i) 5-Methoxy-2-(((4-methoxy-3-methyl-2-pyridinyl)methyl)sulfinyl)-6-methyl-3H-imidazo[4,5-b]pyridine sodium salt

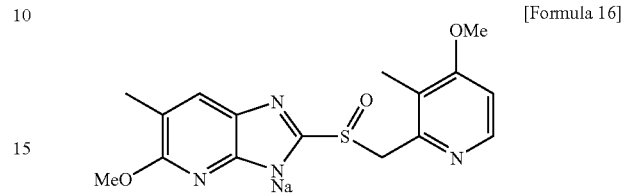

[Formula 16]

5-Methoxy-2-(((4-methoxy-3-methyl-2-pyridinyl)methyl)sulfinyl)-6-methyl-3H-imidazo[4,5-b]pyridine (654 mg, 1.89 mmol) was dissolved in ethanol (30 ml), a 1N sodium hydroxide solution (1.89 ml, 1.89 mmol) was added thereto, and the reaction mixture was stirred for 30 minutes at room temperature. The residue which was obtained by evaporating the solvent was dissolved in ethanol, and the solvent was evaporated again. The obtained residue was suspended in ether, the solvent was evaporated, ether was added again to form a suspension, the solvent was evaporated thereby yielding the title compound (690 mg, 1.87 mmol, 99%) as a white solid.

$^1$H NMR (400 MHz, DMSO-d$_6$) δ ppm; 2.16 (3H, s), 2.19 (3H, s), 3.85 (3H, s), 3.86 (3H, s), 4.39 (1H, d, J=13 Hz), 4.75 (1H, d, J=13 Hz), 6.94 (1H, d, J=6 Hz), 7.54 (1H, s), 8.30 (1H, d, J=6 Hz).

Example 2

2-(((4-Methoxy-3-methyl-2-pyridinyl)methyl]sulfinyl)-6-methyl-5-(2,2,2-trifluoroethoxy)-3H-imidazo[4,5-b]pyridine Sodium salt

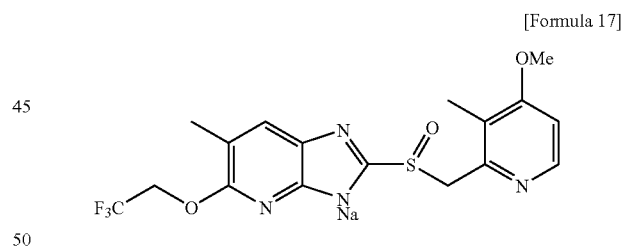

[Formula 17]

(2a) 2-Chloro-3-methylpyridine 1-oxide

[Formula 18]

Into a mixture of 2-chloro-3-methylpyridine (12.8 g, 100 mmol), urea hydrogen peroxide addition compound ((NH$_2$)$_2$CO.H$_2$O$_2$, 19.8 g, 210 mmol) and dichloromethane (130 ml) was added dropwise anhydrous trifluoroacetic acid (28.2 ml, 200 mmol) at 0° C. under nitrogen flow, and the reaction mixture was stirred at 0° C. for 1 hour. Then, after stirring for 30 minutes and elevating the reaction temperature to room temperature, an aqueous solution (200 ml) of sodium hydrosulfite (20 g) was added, and the reaction mixture was stirred for 15 minutes. 2N hydrochloric acid (50 ml) was added and the mixture was extracted with dichloromethane (120 ml), and after washed with sodium bicarbonate solution, the mixture was dried over magnesium sulfate and the solvent was evaporated, thereby yielding the title compound (9.00 g, 62.7 mmol, 63%) as a pale yellow solid.

$^1$H NMR (400 MHz, DMSO-$d_6$) δ ppm; 2.38 (3H, s), 7.29-7.37 (2H, m), 8.30-8.38 (1H, m).

(2b) 2-chloro-5-methylpyridine-1-oxide

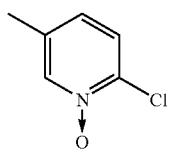

[Formula 19]

Into a mixture of 2-chloro-5-methylpyridine (27.4 g, 215 mmol), urea hydrogen peroxide addition compound (42.5 g, 452 mmol), dichloromethane (250 ml) was added dropwise anhydrous trifluoroacetic acid (60.7 ml and 430 mmol) at 0° C., and the reaction mixture was stirred at 0° C. for 1 hour. Then, after stirring for 45 minutes while elevating the reaction temperature to room temperature, an aqueous solution (450 ml) of sodium hydrosulfite (45 g) was added, and the reaction mixture was stirred for 15 minutes. 0.5N hydrochloric acid (400 ml) was added and the mixture was extracted with dichloromethane (400 ml), and after washed with sodium bicarbonate solution, the mixture was dried over magnesium sulfate and the solvent was evaporated, thereby yielding the title compound (22.5 g, 157 mmol, 73%) as a beige solid.

$^1$H NMR (400 MHz, DMSO-$d_6$) δ ppm; 2.24 (3H, s), 7.16-7.23 (1H, m), 7.66 (1H, d, J=8 Hz), 8.35 (1H, s).

(2c) 2,6-Dichloro-3-methylpyridine

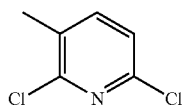

[Formula 20]

(Method 1)

2-Chloro-3-methylpyridine 1-oxide (9.00 g, 62.7 mmol) and triethylamine (10.4 ml, 75.2 mmol) were dissolved in dichloromethane (70 ml), and a solution of phosphorus oxychloride (7 ml, 75.3 mmol) in dichloromethane (40 ml) was added dropwise at 0° C. After stirring for 3 hours while elevating reaction temperature to room temperature, the reaction mixture was stirred under reflux for 1 hour. After the reaction was completed, water (30 ml) was added and the reaction mixture was neutralized with a sodium hydroxide solution, and after extracted with dichloromethane (70 ml), dried over magnesium sulfate. The solvent was evaporated and purified by silica gel column chromatography (eluting solvent: ethyl acetate/n-hexane=3/100), thereby yielding the title compound (3.47 g) as a white solid 10:3 mixture with 2,4-dichloro-3-methylpyridine.

(Method 2)

2-Chloro-5-methylpyridine 1-oxide (22.5 g, 157 mmol) and triethylamine (27.6 ml, 188 mmol) were dissolved in dichloromethane (160 ml), and the dichloromethane (80 ml) solution of phosphorus oxychloride (17.5 ml, 188 mmol) was added dropwise at −10° C. After stirring at −10° C. to 0° C. for 2 hours, stirring was conducted for 1 hour and 35 minutes while elevating reaction temperature to room temperature. After the reaction was completed, water (60 ml) was added thereto and the mixture was neutralized with a sodium hydroxide solution, and the separated organic layer was washed with a saturated brine solution. The aqueous layer of the reaction solution was extracted with ethyl acetate, washed with a saturated brine solution, the organic layer was combined and dried over magnesium sulfate. The solvent was evaporated and purified by silica gel column chromatography (eluting solvent: ethyl acetate/n-hexane), thereby yielding the title compound (17.4 g) as a white solid 10:1.5 mixture with 2,4-dichloro-5-methylpyridine.

$^1$H NMR (400 MHz, DMSO-$d_6$) δ ppm; 2.33 (3H, s), 7.50 (1H, d, J=8 Hz), 7.89 (1H, d, J=8 Hz).

(2d) 2,6-Dichloro-3-methyl-5-nitropyridine

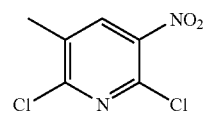

[Formula 21]

Anhydrous trifluoromethanesulfonic acid (21.9 ml, 129 mmol) was dropped into a mixture of tetramethyl ammonium nitrate (17.3 g, 127 mmol) and dichloromethane (60 ml) at 0° C. under nitrogen flow, and the reaction mixture was stirred for 1.5 hours while elevating to room temperature. After a 10:1.5 mixture (13.7 g) of 2,6-dichloro-3-methylpyridine and 2,4-dichloro-5-methylpyridine in dichloromethane (20 ml) was added and stirred for 30 minutes at room temperature, the reaction mixture was stirred under reflux for 48 hours. The reaction mixture was poured into a saturated sodium bicarbonate solution, and extracted with dichloromethane (200 ml), and after washed with water, dried over magnesium sulfate. The residue obtained by evaporating the solvent was triturated with heptane, thereby yielding the title compound (6.55 g, 31.6 mmol) as a pale brown solid.

$^1$H NMR (400 MHz, DMSO-$d_6$) δ ppm; 2.42 (3H, s), 8.70 (1H, s)

(2e) 6-Chloro-5-methyl-3-nitro-2-pyridinamine

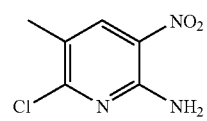

[Formula 22]

A mixture of 2,6-dichloro-3-methyl-5-nitropyridine (10.41 g, 50.3 mmol), 28% aqueous ammonia solution (17 ml, 0.25 mol), potassium carbonate (10.4 g, 75.5 mmol) and t-butanol (167 ml) was stirred overnight at 60° C. under

(2f) 5-Methyl-3-nitro-6-(2,2,2-trifluoroethoxy)-2-pyridinamine

[Formula 23]

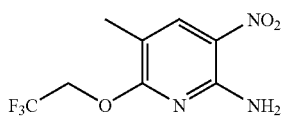

2,2,2-Trifluoroethanol (340 mg, 3.4 mmol) was dissolved in the tetrahydrofuran (10 ml), sodium hydride (60%) (120 mg, 3.0 mmol) was added thereto, and the reaction mixture was stirred for 30 minutes at room temperature under nitrogen atmosphere. A solution of 6-chloro-5-methyl-3-nitro-2-pyridineamine crude product (400 mg) in tetrahydrofuran (10 ml) was dropped, and the reaction mixture was stirred at room temperature for 2.5 days. Water was added to the reaction solution and extracted with ethyl acetate, and after washed with a sodium bicarbonate solution, dried over magnesium sulfate. The residue obtained by evaporating the solvent was purified by silica gel column chromatography (eluting solvent: ethyl acetate/n-hexane=15/85) to yield the title compound (225 mg, 0.90 mmol) as a yellow solid.

$^1$H NMR (400 MHz, DMSO-$d_6$) δ ppm; 2.07 (3H, s), 5.06 (2H, q, J=9 Hz), 8.05 (2H, br s), 8.24 (1H, s).

(2g) 6-Methyl-5-(2,2,2-trifluoroethoxy)-3H-imidazo[4,5-b]pyridine-2-thiol

[Formula 24]

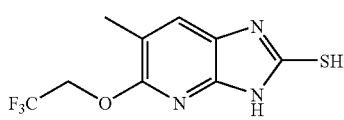

5-Methyl-3-nitro-6-(2,2,2-trifluoroethoxy)-2-pyridineamine (225 mg, 0.90 mmol) was dissolved in methanol (10 ml), 10% Pd-on-carbon powder (50% water content article) (110 mg) was added thereto, and the reaction mixture was stirred under hydrogen atmosphere for 2 hours and 25 minutes. After the reaction was completed, the reaction mixture was filtered through celite, carbon bisulfide (3 ml) was added and stirred at room temperature under nitrogen atmosphere for 2.5 days, and the solvent was then evaporated, thereby yielding the title compound (238 mg, 0.90 mmol) as a white solid.

$^1$H NMR (400 MHz, DMSO-$d_6$) δ ppm; 2.20 (3H, s), 4.94 (2H, q, J=9 Hz), 7.44 (1H, s), 12.60 (1H, br s), 13.00 (1H, br s).

(2h) 2-(((4-Methoxy-3-methyl-2-pyridinyl)methyl)thio)-6-methyl-5-(2,2,2-trifluoroethoxy)-3H-imidazo[4,5-b]pyridine

[Formula 25]

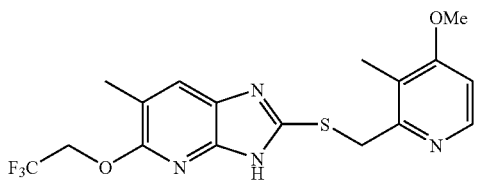

6-Methyl-5-(2,2,2-trifluoroethoxy)-3H-imidazo[4,5-b]pyridine-2-thiol (238 mg, 0.90 mmol) and 2-chloromethyl-4-methoxy-3-methylpyridine hydrochloride salt (243 mg, 1.17 mmol) was dissolved in methanol (20 ml), sodium hydroxide (218 mg, 5.45 mmol) was added thereto, and the mixture was stirred at room temperature overnight. An ammonium chloride solution was added, and the mixture was extracted with chloroform (100 ml), and dried over magnesium sulfate. The residue obtained by evaporating the solvent was purified by silica gel column chromatography (eluting solvent: ethyl acetate/n-hexane=1/1-4/1) to yield the title compound (196 mg, 0.49 mmol, 54%) as a white solid.

$^1$H NMR (400 MHz, DMSO-$d_6$) δ ppm; 2.19 (3H, s), 2.24 (3H, s), 3.85 (3H, s), 4.67 (2H, s), 4.99 (2H, q, J=9 Hz), 6.96 (1H, d, J=6 Hz), 7.72 (1H, br s), 8.24 (1H, d, J=6 Hz).

(2i) 2-(((4-Methoxy-3-methyl-2-pyridinyl)methyl)sulfinyl)-6-methyl-5-(2,2,2-trifluoroethoxy)-3H-imidazo[4,5-b]pyridine

[Formula 26]

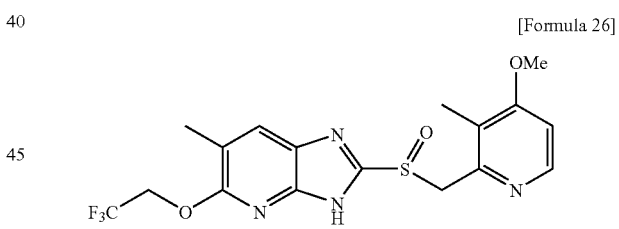

2-(((4-Methoxy-3-methyl-2-pyridinyl)methyl)thio)-6-methyl-5-(2,2,2-trifluoroethoxy)-3H-imidazo[4,5-b]pyridine (270 mg, 0.68 mmol) was dissolved in a mixture of methanol (2 ml) and toluene (18 ml), and a solution of metachloroperbenzoic acid (162 mg) in a mixture of methanol (0.5 ml) of toluene (0.5 ml) were added dropwise at −40° C. under nitrogen flow. After stirred at −20° C. to −40° C. for 2 hours, a sodium bicarbonate solution was added, the mixture was extracted with chloroform (30 ml), and dried over sodium sulfate. The solvent was evaporated, and the solid was precipitated from a mixture of chloroform and n-hexane to yield the title compound (263 mg, 0.63 mmol, 93%) as a purple gray solid.

$^1$H NMR (400 MHz, DMSO-$d_6$) δ ppm; 2.14 (3H, s), 2.28 (3H, s), 3.85 (3H, s), 4.68 (1H, d, J=14 Hz), 4.80 (1H, d, J=14 Hz), 5.04 (2H, q, J=9 Hz), 6.96 (1H, d, J=6 Hz), 7.88 (1H, br s), 8.22 (1H, d, J=6 Hz).

(2j) 2-(((4-Methoxy-3-methyl-2-pyridinyl)methyl)sulfinyl)-6-methyl-5-(2,2,2-trifluoroethoxy)-3H-imidazo[4,5-b]pyridine sodium salt

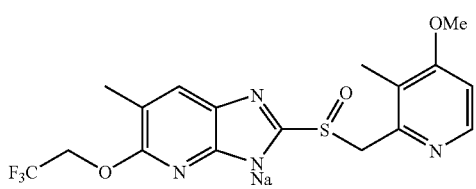

[Formula 27]

2-(((4-Methoxy-3-methyl-2-pyridinyl)methyl)sulfinyl)-6-methyl-5-(2,2,2-trifluoroethoxy)-3H-imidazo[4,5-b]pyridine (263 mg, 0.64 mmol) was suspended in ethanol (30 ml), 1N sodium hydroxide solution (635 μl, 0.64 mmol) was added thereto, and the reaction mixture was stirred for 30 minutes at room temperature. After the solvent was evaporated, ethanol was added and evaporation was conducted again. Ether was added and evaporation was conducted. This operation was repeated twice, thereby yielding the title compound (272 mg, 0.62 mmol, 98%) as a purple gray solid.

$^1$H NMR (400 MHz, DMSO-$d_6$) δ ppm; 2.16 (3H, s), 2.22 (3H, s), 3.84 (3H, s), 4.38 (1H, d, J=13 Hz), 4.78 (1H, d, J=13 Hz), 4.97 (2H, q, J=9 Hz), 6.92 (1H, d, J=6 Hz), 7.61 (1H, s), 8.28 (1H, d, J=6 Hz)

Example 3

5-(2,2-Difluoroethoxy)-2-(((4-methoxy-3-methyl-2-pyridinyl)methyl)sulfinyl)-6-methyl-3H-imidazo[4,5-b]pyridine Sodium salt

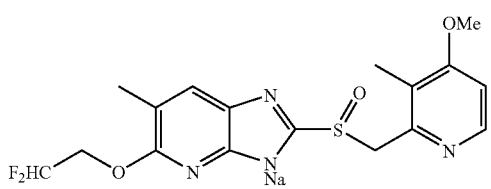

[Formula 28]

(3a) 6-(2,2-difluoroethoxy)-5-methyl-3-nitro-2-pyridineamine

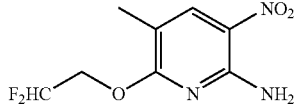

[Formula 29]

2,2-Difluoro ethanol (418 mg, 5.1 mmol) was dissolved in tetrahydrofuran (15 ml), sodium hydride (60%) (180 mg, 4.5 mmol) was added thereto under nitrogen atmosphere, and the reaction mixture was stirred for 30 minutes at room temperature. A solution of 6-chloro-5-methyl-3-nitro-2-pyridineamine (600 mg, 3.20 mmol) in tetrahydrofuran (15 ml) was dropped, and the mixture was stirred at room temperature overnight. Water was added to the reaction solution and extracted with ethyl acetate, and after washed with sodium bicarbonate solution, dried over magnesium sulfate. The residue obtained by evaporating the solvent was triturated with n-hexane to yield the title compound (685 mg, 3.1 mmol, 96%) as an orange solid.

$^1$H NMR (400 MHz, DMSO-$d_6$) δ ppm; 2.05 (3H, s), 4.56-4.69 (2H, m), 6.29-6.60 (1H, m), 8.03 (2H, br s), 8.19 (1H, s).

(3b) 5-(2,2-Difluoroethoxy)-6-methyl-3H-imidazo[4,5-b]pyridine-2-thiol

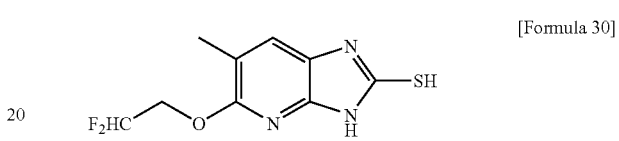

[Formula 30]

6-(2,2-Difluoroethoxy)-5-methyl-3-nitro-2-pyridineamine (685 mg, 3.07 mmol) was dissolved in methanol (30 ml), 10% Pd-on-carbon powder (50% water content article) (300 mg) was added thereto, and the reaction mixture was stirred under hydrogen atmosphere for 2 hours and 30 minutes. After the reaction was completed, the mixture was filtered through celite, carbon bisulfide (7 ml) was added, and the mixture was stirred at room temperature under nitrogen atmosphere for 2.5 days. Thereafter, the solvent was evaporated to yield the title compound (700 mg, 2.85 mmol) as a purple gray solid.

$^1$H NMR (400 MHz, DMSO-$d_6$) δ ppm; 2.18 (3H, s), 4.46-4.59 (2H, m), 6.23-6.54 (1H, m), 7.39 (1H, s), 12.51 (1H, br s), 12.92 (1H, br s).

(3c) 5-(2,2-Difluoroethoxy)-2-(((4-methoxy-3-methyl-2-pyridinyl)methyl)thio)-6-methyl-3H-imidazo[4,5-b]pyridine

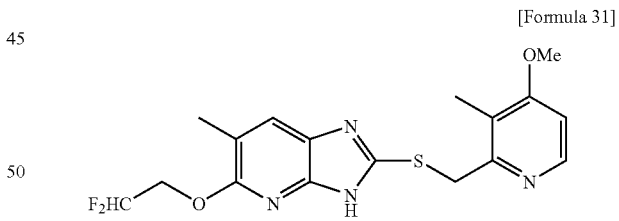

[Formula 31]

5-(2,2-Difluoroethoxy)-6-methyl-3H-imidazo[4,5-b]pyridine-2-thiol (700 mg, 2.85 mmol) and 2-chloromethyl-4-methoxy-3-methylpyridine hydrochloride salt (832 mg, 4.0 mmol) was dissolved in methanol (30 ml), sodium hydroxide (561 mg, 14.0 mmol) was added thereto, and the mixture was stirred overnight at room temperature under nitrogen atmosphere. An ammonium chloride solution was added to the reaction solution, the mixture was extracted with ethyl acetate and chloroform (100 ml), and then dried over magnesium sulfate. The residue obtained by evaporating the solvent was purified by silica gel column chromatography (NH silica gel, eluting solvent: ethyl acetate/n-hexane=1/1-1/0), and triturated with ethanol, thereby yielding the title compound (360 mg, 0.95 mmol, 33%) as a beige solid.

$^1$H NMR (400 MHz, DMSO-d$_6$) δ ppm; 2.19 (3H, s), 2.24 (3H, s), 3.85 (3H, s), 4.53-4.64 (2H, m), 4.67 (2H, s), 6.26-6.57 (1H, m), 6.96 (1H, d, J=6 Hz), 7.68 (1H, br s), 8.24 (1H, d, J=6 Hz).

(3d) 5-(2,2-Difluoroethoxy)-2-(((4-methoxy-3-methyl-2-pyridinyl)methyl)sulfinyl)-6-methyl-3H-imidazo[4,5-b]pyridine

[Formula 32]

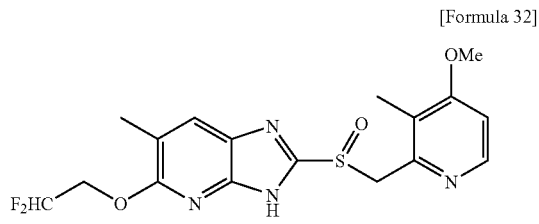

5-(2,2-Difluoroethoxy)-2-(((4-methoxy-3-methyl-2-pyridinyl)methyl)thio)-6-methyl-3H-imidazo[4,5-b]pyridine (150 mg, 0.39 mmol) was dissolved in a mixture of methanol (1.5 ml) and toluene (13.5 ml) and a solution of metachloroperbenzoic acid (94 mg) in a mixture of methanol (0.5 ml) and toluene (0.5 ml) were added dropwise thereto at −40° C. under nitrogen flow.

After stirred at −20° C. to −40° C. for 2 hours, a sodium bicarbonate solution was added, the organic layer was separated, and the aqueous layer was extracted with chloroform (20 ml), and the organic layer was combined and dried over sodium sulfate. The solvent was evaporated, and the solid was then precipitated from a mixture of chloroform, ether and n-hexane, thereby yielding the title compound (134 mg, 0.34 mmol, 86%) as a pale blue solid.

$^1$H NMR (400 MHz, DMSO-d$_6$) δ ppm; 2.13 (3H, s), 2.28 (3H, s), 3.85 (3H, s), 4.56-4.69 (2H, m), 4.72 (1H, d, J=14 Hz), 4.79 (1H, d, J=14 Hz), 6.28-6.60 (1H, m), 6.95 (1H, d, J=6 Hz), 7.88 (1H, br s), 8.20 (1H, d, J=6 Hz).

(3e) 5-(2,2-Difluoroethoxy)-2-(((4-methoxy-3-methyl-2-pyridinyl)methyl)sulfinyl)-6-methyl-3H-imidazo[4,5-b]pyridine sodium salt

[Formula 33]

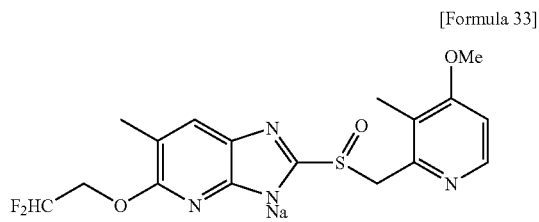

5-(2,2-Difluoroethoxy)-2-(((4-methoxy-3-methyl-2-pyridinyl)methyl)sulfinyl]-6-methyl-3H-imidazo[4,5-b]pyridine (286 mg, 0.72 mmol) was made to suspend in ethanol (10 ml). The mixture of a 1N sodium hydroxide solution (720 μl, 0.72 mmol) and ethanol (3 ml) was added, and the reaction mixture was stirred for 20 minutes at room temperature. After the solvent was evaporated, ethanol was added and evaporation was conducted again, ether was added and evaporation was conducted. This operation was repeated twice, thereby yielding the title compound (277 mg, 0.66 mmol, 92%) as a beige solid.

$^1$H NMR (400 MHz, DMSO-d$_6$) δ ppm; 2.16 (3H, s), 2.21 (3H, s), 3.85 (3H, s), 4.38 (1H, d, J=13 Hz), 4.56 (2H, dt, J=4, 15 Hz), 4.78 (1H, d, J=13 Hz), 6.42 (1H, tt, J=4, 55 Hz), 6.94 (1H, d, J=6 Hz), 7.60 (1H, s), 8.30 (1H, d, J=6 Hz).

Example 4

Optical isomers of 5-methoxy-2-(((4-methoxy-3-methyl-2-pyridinyl)methyl)sulfinyl)-6-methyl-3H-imidazo[4,5-b]pyridine

[Formula 34]

5-Methoxy-2-(((4-methoxy-3-methyl-2-pyridinyl)methyl)sulfinyl]-6-methyl-3H-imidazo[4,5-b]pyridine (racemate) (360 mg) was prepared into a solution containing 3-4.5 mg of the racemate per ml of ethanol/n-hexane=3/2 and fractionated by HPLC (column: CHIRALPAK AD-H 2 cmφ×25 cm (Daicel Chemical Ind., Ltd.), Temperature: about 22° C., Mobile phase: ethanol/n-hexane=3/2, and Flow rate: 9 ml/min, Detection wavelength: 254 nm, 15 mg-22.5 mg/5 ml injected per time). Fractions of an optical isomer having longer retention time and of an optical isomer having shorter retention time were collected, respectively, and were condensed. The title compound having shorter retention time (128 mg, 0.37 mmol) and the title compound having longer retention time (116 mg, 0.33 mmol) were thus obtained as beige solids, respectively.

Title compound having shorter retention time:
$^1$H NMR (400 MHz, DMSO-d$_6$) δ ppm; 2.14 (3H, s), 2.25 (3H, s), 3.85 (3H, s), 3.94 (3H, s), 4.71 (1H, d, J=14 Hz), 4.81 (1H, br d, J=14 Hz), 6.96 (1H, d, J=6 Hz), 7.82 (1H, br s), 8.22 (1H, d, J=6 Hz).

Title compound having longer retention time:
$^1$H NMR (400 MHz, DMSO-d$_6$) δ ppm; 2.14 (3H, s), 2.25 (3H, s), 3.85 (3H, s), 3.94 (3H, s), 4.71 (1H, d, J=14 Hz), 4.81 (1H, br d, J=14 Hz), 6.96 (1H, d, J=6 Hz), 7.82 (1H, br s), 8.22 (1H, d, J=6 Hz).

Example 5

Optical isomers of 5-(2,2-difluoroethoxy)-2-(((4-methoxy-3-methyl-2-pyridinyl)methyl)sulfinyl)-6-methyl-3H-imidazo[4,5-b]pyridine

[Formula 35]

5-(2,2-Difluoroethoxy)-2-(((4-methoxy-3-methyl-2-pyridinyl)methyl)sulfinyl)-6-methyl-3H-imidazo[4,5-b]pyridine (racemate) (350 mg) was prepared into a solution containing 5 mg of the racemate per ml of ethanol/n-hexane=1/4 (0.1% diethylamine content) and fractionated by HPLC (column: CHIRALPAK AD-H 2 cmφ×25 cm (Daicel Chemical Ind., Ltd.), Temperature: about 22° C., Mobile phase:ethanol/n-hexane=1/4 (0.1% diethylamine content), Flow rate: 9 ml/min, Detection wavelength: 254 nm, 20 mg/4 ml were injected per time). Fractions of an optical isomer having longer retention time and of an optical isomer having shorter retention time were collected, respectively, and were condensed, thereby yielding the title compound having shorter retention time (125 mg, 0.32 mmol) and the title compound having longer retention time (107 mg, 0.27 mmol) as beige color solids, respectively.

Title compound having shorter retention time:

$^1$H NMR (400 MHz, DMSO-$d_6$) δ ppm; 2.14 (3H, s), 2.27 (3H, s), 3.85 (3H, s), 4.56-4.69 (2H, m), 4.68 (1H, d, J=14 Hz), 4.79 (1H, d, J=14 Hz), 6.28-6.60 (1H, m), 6.95 (1H, d, J=6 Hz), 7.84 (1H, br s), 8.21 (1H, d, J=6 Hz).

Title compound having longer retention time:

$^1$H NMR (400 MHz, DMSO-$d_6$) δ ppm; 2.14 (3H, s), 2.27 (3H, s), 3.85 (3H, s), 4.56-4.69 (2H, m), 4.68 (1H, d, J=14 Hz), 4.80 (1H, d, J=14 Hz), 6.28-6.60 (1H, m), 6.95 (1H, d, J=6 Hz), 7.84 (1H, br s), 8.21 (1H, d, J=6 Hz).

Example 6

Sodium Salt of an Optical Isomer Having Shorter Retention Time of 5-methoxy-2-(((4-methoxy-3-methyl-2-pyridinyl)methyl)sulfinyl)-6-methyl-3H-imidazo[4,5-b]pyridine

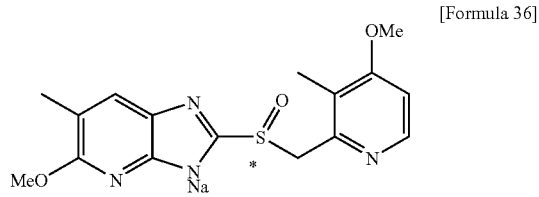

[Formula 36]

5-Methoxy-2-(((4-methoxy-3-methyl-2-pyridinyl)methyl)sulfinyl)-6-methyl-3H-imidazo[4,5-b]pyridine in the form of an optical isomer having shorter retention time (124 mg, 0.36 mmol) was dissolved in ethanol (20 ml) and a mixed solution of 1N sodium hydroxide solution (0.36 ml, 0.36 mmol) and ethanol (2 ml) was added thereto and the reaction mixture was stirred for 30 minutes at room temperature. The residue which was obtained by evaporating the solvent was dissolved in ethanol, and the solvent was evaporated again. Ether was added to the resulting residue to form a suspension, ether was evaporated, and ether was added again to form a suspension and the solvent was evaporated, thereby yielding the title compound (133 mg, 0.36 mmol) as a beige solid.

$^1$H NMR (400 MHz, DMSO-$d_6$) δ ppm; 2.16 (3H, s), 2.18 (3H, s), 3.85 (3H, s), 3.86 (3H, s), 4.36 (1H, d, J=13 Hz), 4.80 (1H, d, J=13 Hz), 6.92 (1H, d, J=6 Hz), 7.52 (1H, s), 8.28 (1H, d, J=6 Hz).

Example 7

Sodium Salt of an Optical Isomer Having Longer Retention Time of 5-methoxy-2-(((4-methoxy-3-methyl-2-pyridinyl)methyl)sulfinyl)-6-methyl-3H-imidazo[4,5-b]pyridine

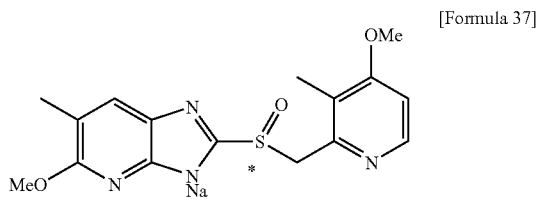

[Formula 37]

5-Methoxy-2-(((4-methoxy-3-methyl-2-pyridinyl)methyl)sulfinyl)-6-methyl-3H-imidazo[4,5-b]pyridine in the form of an optical isomer having longer retention time (83 mg, 0.24 mmol) was dissolved in ethanol (15 ml) and a mixed solution of 1N sodium hydroxide solution (0.24 ml, 0.24 mmol) and ethanol (2 ml) was added, and the reaction mixture was stirred for 30 minutes at room temperature. The residue which was obtained by evaporating the solvent was dissolved in ethanol, and the solvent was evaporated again. Ether was added to the resulting residue to form a suspension, ether was evaporated, and ether was added again to form a suspension and the solvent was evaporated, thereby yielding the title compound (88 mg, 0.24 mmol) as a beige solid.

$^1$H NMR (400 MHz, DMSO-$d_6$) δ ppm; 2.16 (3H, s), 2.18 (3H, s), 3.84 (3H, s), 3.85 (3H, s), 4.36 (1H, d, J=13 Hz), 4.80 (1H, d, J=13 Hz), 6.92 (1H, d, J=6 Hz), 7.51 (1H, s), 8.28 (1H, d, J=6 Hz).

Example 8

Sodium Salt of an Optical Isomer Having Shorter Retention Time of 5-(2,2-difluoroethoxy)-2-(((4-methoxy-3-methyl-2-pyridinyl)methyl)sulfinyl)-6-methyl-3H-imidazo[4,5-b]pyridine

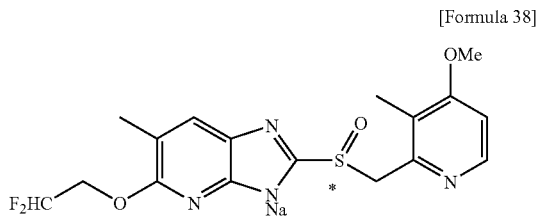

[Formula 38]

5-(2,2-Difluoroethoxy)-2-(((4-methoxy-3-methyl-2-pyridinyl)methyl)sulfinyl)-6-methyl-3H-imidazo[4,5-b]pyridine in the form of an optical isomer having shorter retention time (125 mg, 0.32 mmol) was dissolved in ethanol (20 ml) and a mixed solution of 1N sodium hydroxide solution (0.32 ml, 0.32 mmol) and ethanol (5 ml) were added, and the reaction mixture was stirred for 30 minutes at room temperature. The residue which was obtained by evaporating the solvent was dissolved in ethanol, and the solvent was evaporated again. Ether was added to the resulting residue to form a suspension, and the solvent was evaporated, thereby yielding the title compound (122 mg, 0.29 mmol) as a beige solid.

¹H NMR (400 MHz, DMSO-d₆) δ ppm; 2.16 (3H, s), 2.21 (3H, s), 3.84 (3H, s), 4.37 (1H, d, J=13 Hz), 4.55 (2H, dt, J=4, 15 Hz), 4.78 (1H, d, J=13 Hz), 6.42 (1H, tt, J=4, 55 Hz), 6.93 (1H, d, J=6 Hz), 7.58 (1H, s), 8.28 (1H, d, J=6 Hz).

Example 9

Sodium Salt of an Optical Isomer Having Longer Retention Time of 5-(2,2-difluoroethoxy)-2-(((4-methoxy-3-methyl-2-pyridinyl)methyl)sulfinyl)-6-methyl-3H-imidazo[4,5-b]pyridine

[Formula 39]

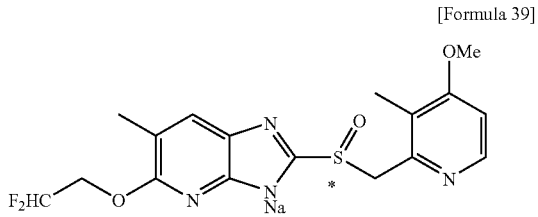

5-(2,2-Difluoroethoxy)-2-(((4-methoxy-3-methyl-2-pyridinyl)methyl)sulfinyl)-6-methyl-3H-imidazo[4,5-b]pyridine in the form of an optical isomer having longer retention time (107 mg, 0.27 mmol) was dissolved in ethanol (20 ml) and a mixed solution of 1N sodium hydroxide solution (0.27 ml, 0.27 mmol) and ethanol (5 ml) were added, and the reaction mixture was stirred for 30 minutes at room temperature. The residue which was obtained by evaporating the solvent was dissolved in ethanol, and the solvent was evaporated again. Ether was added to the resulting residue to form a suspension, and the solvent was evaporated, thereby yielding the title compound (99 mg, 0.24 mmol) as a beige solid.

¹H NMR (400 MHz, DMSO-d₆) δ ppm; 2.16 (3H, s), 2.21 (3H, s), 3.84 (3H, s), 4.38 (1H, d, J=13 Hz), 4.55 (2H, dt, J=4, 15 Hz), 4.79 (1H, d, J=13 Hz), 6.41 (1H, tt, J=4, 55 Hz), 6.92 (1H, d, J=6 Hz), 7.59 (1H, s), 8.28 (1H, d, J=6 Hz).

Example 10

Sodium Salt of 5-(4-fluorophenoxy)-2-(((4-methoxy-3-methyl-2-pyridinyl)methyl)sulfinyl)-3H-imidazo[4,5-b]pyridine

[Formula 40]

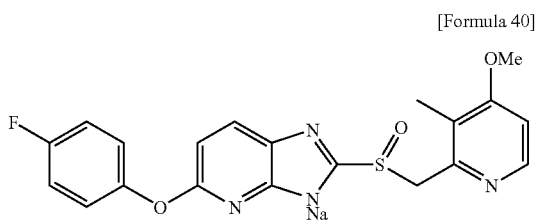

¹H NMR (400 MHz, DMSO-d₆) δ ppm; 2.15 (3H, s), 3.84 (3H, s), 4.40 (1H, d, J=13 Hz), 4.70 (1H, d, J=13 Hz), 6.59 (1H, d, J=8 Hz), 6.94 (1H, d, J=6 Hz), 6.93-7.11 (2H, m), 7.16-7.21 (2H, m), 7.84 (1H, d, J=8 Hz), 8.29 (1H, d, J=6 Hz)

Example 11

Sodium Salt of 5-(3-fluorophenoxy)-2-(((4-methoxy-3-methyl-2-pyridinyl)methyl)sulfinyl)-3H-imidazo[4,5-b]pyridine

[Formula 41]

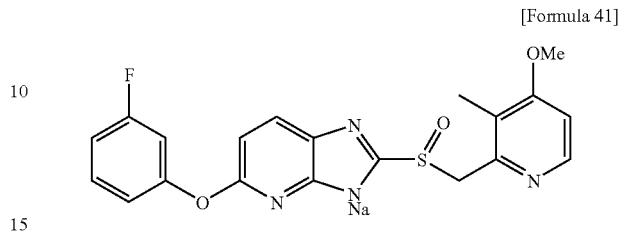

¹H NMR (400 MHz, DMSO-d₆) δ ppm; 2.14 (3H, s), 3.83 (3H, s), 4.41 (1H, d, J=13 Hz), 4.70 (1H, d, J=13 Hz), 6.63 (1H, d, J=8 Hz), 6.86-6.94 (4H, m), 7.37 (1H, q, J=8 Hz), 7.86 (1H, d, J=8 Hz), 8.29 (1H, d, J=6 Hz)

Example 12

Sodium Salt of 2-(((4-methoxy-3-methyl-2-pyridinyl)methyl)sulfinyl)5-(4-methoxyphenoxy)-6-methyl-3H-imidazo[4,5-b]pyridine

[Formula 42]

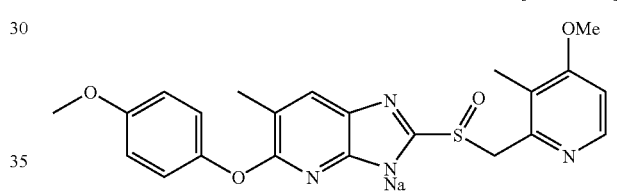

¹H NMR (400 MHz, DMSO-d₆) δ ppm; 2.14 (3H, s), 2.30 (3H, s), 3.74 (3H, s), 3.84 (3H, s), 4.35 (1H, d, J=13 Hz), 4.74 (1H, d, J=13 Hz), 6.86-6.97 (5H, m), 7.65 (1H, s), 8.28 (1H, d, J=6 Hz)

Example 13

Sodium Salt of 2-(((4-methoxy-3-methyl-2-pyridinyl)methyl)sulfinyl)5-(2-phenoxyethoxy)-3H-imidazo[4,5-b]pyridine

[Formula 43]

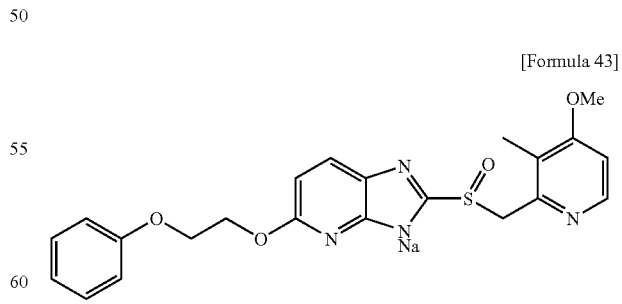

¹H NMR (400 MHz, DMSO-d₆) δ ppm; 2.18 (3H, s), 3.85 (3H, s), 4.30-4.36 (2H, m), 4.39 (1H, d, J=13 Hz), 4.55-4.62 (2H, m), 4.80 (1H, d, J=13 Hz), 6.38 (1H, d, J=8 Hz), 6.92-6.97 (2H, m), 6.98-7.03 (2H, m), 7.27-7.33 (2H, m), 7.71 (1H, d, J=8 Hz), 8.30 (1H, d, J=6 Hz).

Example 14

Sodium Salt of 5-(2-(4-fluorophenyl)ethoxy)-2-(((4-methoxy-3-methyl-2-pyridinyl)methyl)sulfinyl)-3H-imidazo[4,5-b]pyridine

[Formula 44]

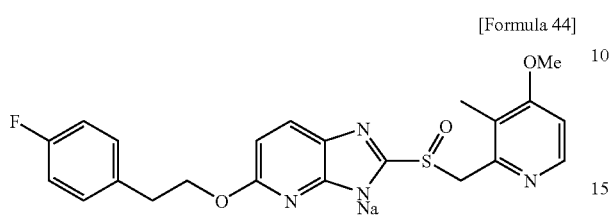

¹H NMR (400 MHz, DMSO-d$_6$) δ ppm; 2.17 (3H, s), 3.04 (2H, t, J=7 Hz), 3.85 (3H, s), 4.38 (1H, d, J=13 Hz), 4.44 (2H, t, J=7 Hz), 4.78 (1H, d, J=13 Hz), 6.31 (1H, d, J=8 Hz), 6.94 (1H, d, J=6 Hz), 7.10-7.17 (2H, m), 7.33-7.39 (2H, m), 7.68 (1H, d, J=8 Hz), 8.30 (1H, d, J=6 Hz).

Example 15

Sodium Salt of 2-(((4-methoxy-3-methyl-2-pyridinyl)methyl)sulfinyl)-5-(2-phenylpropoxy)-3H-imidazo[4,5-b]pyridine

[Formula 45]

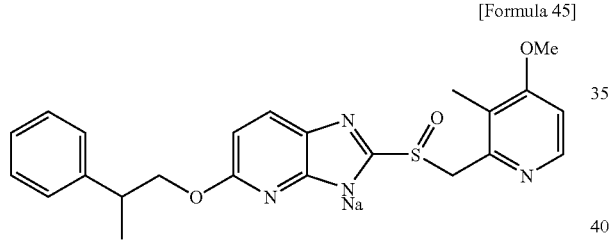

¹H NMR (400 MHz, DMSO-d$_6$) δ ppm; 1.30 (3H, d, J=7 Hz), 2.15 (3H, s), 3.18-3.28 (1H, m), 3.38 (3H, s), 4.25-4.40 (2H, m), 4.37 (1H, d, J=13 Hz), 4.75 (1H, d, J=13 Hz), 6.27 (1H, d, J=8 Hz), 6.92 (1H, d, J=6 Hz), 7.17-7.23 (1H, m), 7.28-7.34 (4H, m), 7.64 (1H, d, J=8 Hz), 8.28 (1H, d, J=6 Hz).

Example 16

Sodium Salt of 5-(2,2-difluoroethoxy)-6-ethyl-2-(((4-methoxy-3-methyl-2-pyridinyl)methyl)sulfinyl)-3H-imidazo[4,5-b]pyridine

[Formula 46]

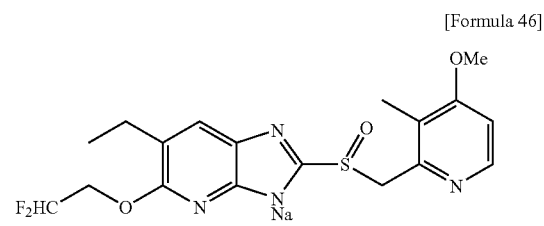

¹H NMR (400 MHz, DMSO-d$_6$) δ ppm; 1.17 (3H, t, J=7 Hz), 2.17 (3H, s), 2.60 (2H, q, J=7 Hz), 3.84 (3H, s), 4.37 (1H, d, J=13 Hz), 4.51-4.60 (2H, m), 4.76 (1H, d, J=13 Hz), 6.41 (1H, tt, J=4, 55 Hz), 6.93 (1H, d, J=6 Hz), 7.58 (1H, s), 8.28 (1H, d, J=6 Hz)

Example 17

Sodium Salt of 5-(2,2-difluoroethoxy)-2-(((4-methoxy-3-methyl-2-pyridinyl)methyl)sulfinyl)-6-propyl-3H-imidazo[4,5-b]pyridine

[Formula 47]

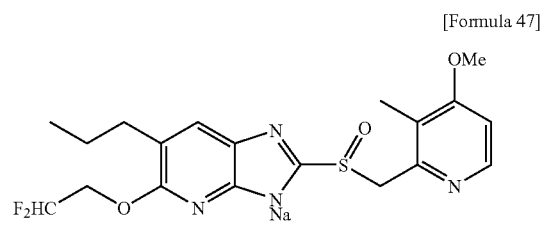

1H NMR (400 MHz, DMSO-d$_6$) δ ppm; 0.90 (3H, t, J=7 Hz), 1.59 (2H, sex, J=7 Hz), 2.17 (3H, s), 2.57 (2H, t, J=7 Hz), 3.84 (3H, s), 4.37 (1H, d, J=13 Hz), 4.55 (2H, dt, J=4, 15 Hz), 4.76 (1H, d, J=13 Hz), 6.40 (1H, tt, J=4, 55 Hz), 6.93 (1H, d, J=6 Hz), 7.56 (1H, s), 8.29 (1H, d, J=6 Hz).

Example 18

Sodium Salt of 2-(((3-ethyl-4-methoxy-2-pyridinyl)methyl)sulfinyl)-(5-methoxy-6-methyl-3H-imidazo[4,5-b]pyridine

[Formula 48]

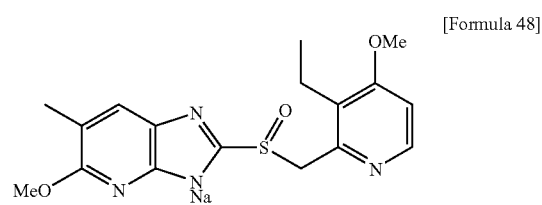

¹H NMR (400 MHz, DMSO-d$_6$) δppm; 1.07 (3H, t, J=8 Hz), 2.18 (3H, s), 2.60-2.83 (2H, m), 3.86 (6H, s), 4.33 (1H, d, J=13 Hz), 4.76 (1H, d, J=13 Hz), 6.96 (1H, d, J=6 Hz), 7.54 (1H, s), 8.32 (1H, d, J=6 Hz).

Example 19

Sodium Salt of 5-(2-butynyloxy)-2-(((4-methoxy-3-methyl-2-pyridinyl)methyl)sulfinyl)-6-methyl-3H-imidazo[4,5-b]pyridine

[Formula 49]

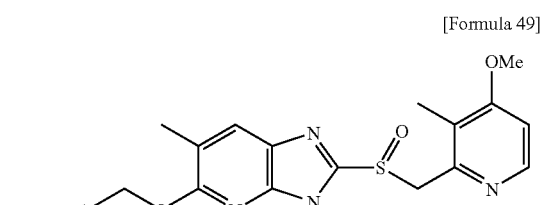

¹H NMR (400 MHz, DMSO-d$_6$) δ ppm; 1.03 (3H, t, J=2 Hz), 2.17 (3H, s), 2.19 (3H, s), 3.85 (3H, s), 4.36 (1H, d, J=13 Hz), 4.80 (1H, d, J=13 Hz), 4.93 (2H, q, J=2 Hz), 6.93 (1H, d, J=6 Hz), 7.55 (1H, s), 8.29 (1H, d, J=6 Hz).

Example 20

2-[[(4-Methoxy-3-methyl-2-pyridinyl)methyl]sulfinyl]-5-(3-pentynyloxy)-3H-imidazo[4,5-b]pyridine sodium salt

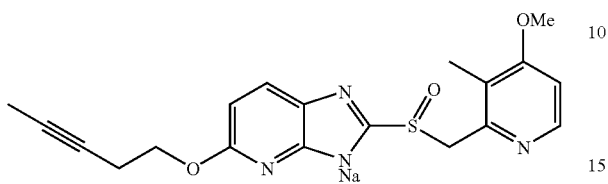

$^1$H NMR (400 MHz, DMSO-d$_6$) δ ppm; 1.76 (3H, t, J=2 Hz), 2.16 (3H, s), 2.52-2.62 (2H, m), 3.84 (3H, s), 4.28 (2H, t, J=7 Hz), 4.38 (1H, d, J=13 Hz), 4.75 (1H, d, J=13 Hz), 6.32 (1H, d, J=8 Hz), 6.93 (1H, d, J=6 Hz), 7.67 (1H, d, J=8 Hz), 8.28 (1H, d, J=6 Hz).

Example 21

5-Ethoxy-2-[[(4-methoxy-3-methyl-2-pyridinyl)methyl]sulfinyl]-6-methyl-3H-imidazo[4,5-b]pyridine sodium salt

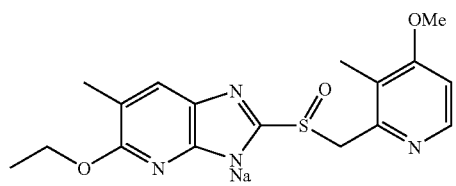

$^1$H NMR (400 MHz, DMSO-d$_6$) δ ppm; 1.34 (3H, t, J=7 Hz), 2.16 (3H, s), 2.17 (3H, s), 3.85 (3H, s), 4.31 (2H, q, J=7 Hz), 4.37 (1H, d, J=13 Hz), 4.78 (1H, d, J=13 Hz), 6.94 (1H, d, J=6 Hz), 7.52 (1H, s), 8.30 (1H, d, J=6 Hz).

Example 22

5-Isopropoxy-2-[[(4-methoxy-3-methyl-2-pyridinyl)methyl]sulfinyl]-6-methyl-3H-imidazo[4,5-b]pyridine sodium salt

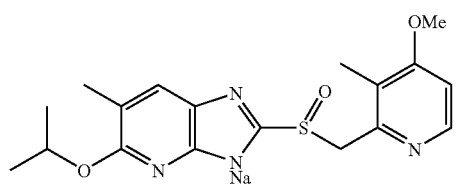

$^1$H NMR (400 MHZ, DMSO-d$_6$) δ ppm; 1.29 (6H, d, J=6 Hz), 2.13 (3H, s), 2.15 (3H, s), 3.83 (3H, s), 4.35 (1H, d, J=13 Hz), 4.77 (1H, d, J=13 Hz), 5.27 (1H, hept, J=6 Hz), 6.92 (1H, d, J=6 Hz), 7.49 (1H, s), 8.28 (1H, d, J=6 Hz).

Example 23

5-(Cyclopropylmethoxy)-2-[[(4-methoxy-3-methyl-2-pyridinyl)methyl]sulfinyl]-6-methyl-3H-imidazo[4,5-b]pyridine sodium salt

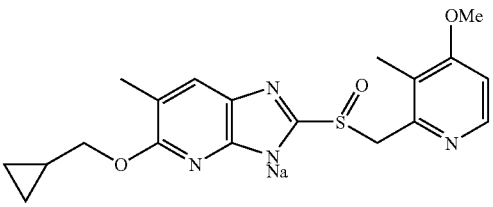

$^1$H NMR (400 MHz, DMSO-d$_6$) δ ppm; 0.32-0.36 (2H, m), 0.51-0.56 (2H, m), 1.24-1.34 (1H, m), 2.16 (3H, s), 2.20 (3H, s), 3.84 (3H, s), 4.12 (2H, d, J=7 Hz), 4.38 (1H, d, J=13 Hz), 4.80 (1H, d, J=13 Hz), 6.93 (1H, d, J=6 Hz), 7.53 (1H, s), 8.29 (1H, d, J=6 Hz).

Example 24

5-(2-Butynyloxy)-2-[[(4-methoxy-3-methyl-2-pyridinyl)methyl]sulfinyl]-3H-imidazo[4,5-b]pyridine sodium salt

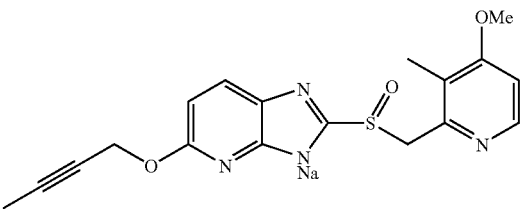

$^1$H NMR (400 MHz, DMSO-d$_6$) δ ppm; 1.81 (3H, t, J=2 Hz), 2.15 (3H, s), 3.83 (3H, s), 4.36 (1H, d, J=13 Hz), 4.76 (1H, d, J=13 Hz), 4.85-4.90 (2H, m), 6.34 (1H, d, J=8 Hz), 6.93 (1H, d, J=6 Hz), 7.69 (1H, d, J=8 Hz), 8.28 (1H, d, J=6 Hz).

Example 25

2-[[(4-Methoxy-3-methyl-2-pyridinyl)methyl]sulfinyl]-5-methoxy-6-methyl-3H-imidazo[4,5-b]pyridine sodium salt

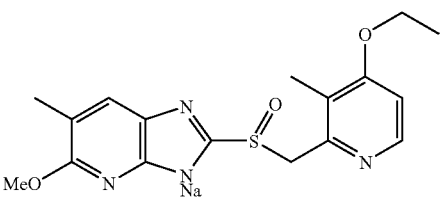

$^1$H NMR (400 MHz, DMSO-d$_6$) δ ppm; 1.36 (3H, t, J=7 Hz), 2.16 (3H, s), 2.18 (3H, s), 3.86 (3H, s), 4.10 (2H, q, J=7 Hz), 4.37 (1H, d, J=13 Hz), 4.78 (1H, d, J=13 Hz), 6.91 (1H, d, J=6 Hz), 7.53 (1H, s), 8.27 (1H, d, J=6 Hz).

Example 26

2-[[(4-Methoxy-3-methyl-2-pyridinyl)methyl]sulfinyl]-6-methyl-5-(2-fluoroethoxy)-3H-imidazo[4,5-b]pyridine sodium salt

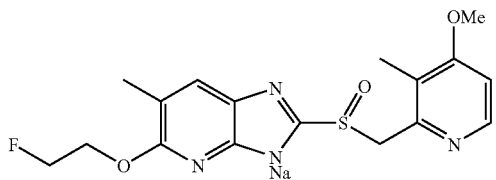

$^1$H NMR (400 MHz, DMSO-$d_6$) δ ppm; 2.16 (3H, s), 2.20 (3H, s), 3.84 (3H, s), 4.37 (1H, d, J=13 Hz), 4.46-4.50 (1H, m), 4.54-4.58 (1H, m), 4.70-4.74 (1H, m), 4.79 (1H, d, J=13 Hz), 4.82-4.86 (1H, m), 6.93 (1H, d, J=5 Hz), 7.56 (1H, s), 8.29 (1H, d, J=5 Hz).

Example 27

2-[[(4-Methoxy-3-methyl-2-pyridinyl)methyl]sulfinyl]-6-methyl-5-propoxy-3H-imidazo[4,5-b]pyridine sodium salt

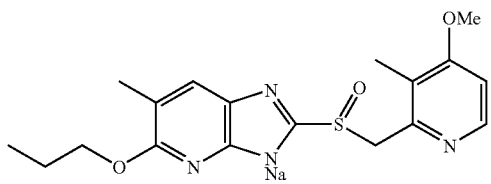

$^1$H NMR (400 MHz, DMSO-$d_6$) δ ppm; 1.00 (3H, t, J=7 Hz), 1.71-1.79 (2H, m), 2.16 (3H, s), 2.18 (3H, s), 3.84 (3H, s), 4.22 (2H, t, J=7 Hz), 4.37 (1H, d, J=13 Hz), 4.80 (1H, d, J=13 Hz), 6.93 (1H, d, J=6 Hz), 7.52 (1H, s), 8.29 (1H, d, J=6 Hz).

Example 28

5-Isobutoxy-2-[[(4-methoxy-3-methyl-2-pyridinyl)methyl]sulfinyl]-6-methyl-3H-imidazo[4,5-b]pyridine sodium salt

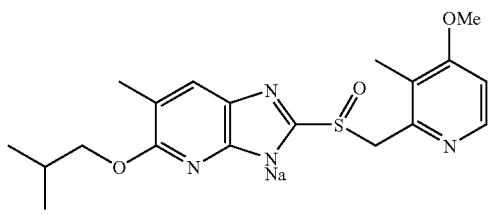

$^1$H NMR (400 MHz, DMSO-$d_6$) δ ppm; 1.01 (6H, d, J=7 Hz), 2.01-2.12 (1H, m), 2.16 (3H, s), 2.19 (3H, s), 3.85 (3H, s), 4.04 (2H, d, J=7 Hz), 4.37 (1H, d, J=13 Hz), 4.81 (1H, d, J=13 Hz), 6.93 (1H, d, J=5 Hz), 7.52 (1H, d, J=1 Hz), 8.29 (1H, d, J=5 Hz).

Example 29

5-(Cyclohexyloxy)-2-[[(4-methoxy-3-methyl-2-pyridinyl)methyl]sulfinyl]-6-methyl-3H-imidazo[4,5-b]pyridine sodium salt

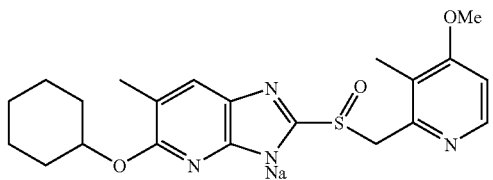

$^1$H NMR (400 MHz, DMSO-$d_6$) δ ppm; 1.29-1.59 (6H, m), 1.70-1.79 (2H, m), 1.91-2.00 (2H, m), 2.17 (3H, s), 2.17 (3H, d, J=1 Hz), 3.85 (6H, s), 4.38 (1H, d, J=13 Hz), 4.81 (1H, d, J=13 Hz), 5.04-5.12 (1H, m), 6.93 (1H, d, J=6 Hz), 7.53 (1H, d, J=1 Hz), 8.29 (1H, d, J=6 Hz).

Preparation Example 1

6-Methoxy-3-nitro-2-pyridineamine

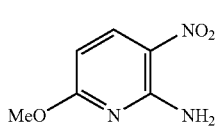

[Formula 50]

A solution of 2-chloro-6-methoxy-3-nitropyridine (25.3 g, 0.134 mol) and a concentrated aqueous ammonia solution (70 ml) in N,N-dimethylformamide (200 ml) was stirred at 70° C. for 4 hours and 15 minutes. The reaction mixture was cooled to room temperature and then diluted with water. The resulted precipitate was collected by filtration to yield the title compound (16.8 g, 99.2 mmol, 74.0%) as a yellow solid.

$^1$H NMR (400 MHz, DMSO-$d_6$) δppm; 3.90 (3H, s), 6.16 (1H, d, J=9 Hz), 8.16 (2H, br s), 8.26 (1H, d, J=9 Hz).

Preparation Example 2

5-Iodo-6-methoxy-3-nitro-2-pyridineamine

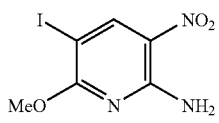

[Formula 51]

A suspension of 6-methoxy-3-nitro-2-pyridineamine (14.6 g, 86.4 mmol) and N-iodosuccinimide (29.2 g, 130 mmol) in acetic acid (280 ml) was stirred at room temperature for 21 hours and 30 minutes. The reaction mixture was concentrated and the residue was dissolved in ethyl acetate and 0.5N sodium hydroxide. The ethyl acetate layer was washed with a saturated sodium bicarbonate solution and a saturated brine solution, dried over anhydrous sodium sulfate, and concentrated. The residue was suspended in hexane, and a resulted precipitate was filtered and washed with hexane, thereby yielding the title compound (25.2 g, 85.5 mmol, 98.9%) as a yellow solid.

$^1$H NMR (400 MHz, DMSO-$d_6$) δppm; 3.91 (3H, s), 8.20 (2H, br s), 8.54 (1H, s).

Preparation Example 3

6-Methoxy-5-methyl-3-nitro-2-pyridineamine

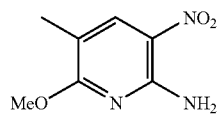

[Formula 52]

A mixture of 5-iodo-6-methoxy-3-nitro-2-pyridineamine (1.03 g, 3.49 mmol), trimethylboroxin (456 mg, 3.63 mmol), cesium carbonate (3.56 g, 10.9 mmol), tetrakis(triphenylphosphine)palladium(0) (412 mg, 0.357 mmol) and N,N-dimethylformamide (10 ml) was stirred at 90° C. under nitrogen atmosphere. After 2 hours and 30 minutes, trimethylboroxin (500 μl, 3.58 mmol) was added, and the reaction mixture was further stirred under the same conditions for 5 hours and 30 minutes. The reaction mixture was cooled to room temperature and then diluted with ethyl acetate and water. Insoluble substance was filtered off, the organic layer of the filtrate was washed 3 times with a saturation ammonium chloride solution, dried over anhydrous sodium sulfate, filtered and concentrated. The residue was purified by silica gel column chromatography (silica gel: 40 g, eluting solvent: heptane, heptane/ethyl acetate=90/10) to yield the title compound (350 mg, 1.91 mmol, 54.8%) as a yellow solid.

$^1$H NMR (400 MHz, DMSO-$d_6$) δppm; 2.03 (3H, s), 3.93 (3H, s), 8.02 (2H, br s), 8.11 (1H, s).

Test Example 1

Inhibitory Effects on Gastric Acid Secretion in Rats

Seven-week-old male SD rats fasted from the day before experiments were used. The rats were subjected to celiotomy along the median line under ether anesthesia, and the pylorus was ligated. Test compounds were dissolved or suspended in 0.5% methyl-cellulose solution (solvent) and prepared the concentration of 5 mg/ml. Histamine was dissolved in brine (solvent) and prepared the concentration of 10 mg/ml. 0.5% methyl-cellulose solution or test compound solution (10 mg/kg) in a volume of 0.2 ml per 100 g body weight was injected into the duodenum at the time of ligation, and then histamine solution (20 mg/kg) in a volume of 0.2 ml per 100 g body weight was administered subcutaneously. Then the abdomen was sutured.

Eight hours after the administration of solvent or test compound, rat was sacrificed and stomach was isolated for the measurement of the volume of gastric juice. After the volume of gastric juice was determined, the acid concentration was measured using 0.25 ml of gastric juice by titration against 0.04 mol/l NaOH solution to pH 7.0. The acid output was calculated as (volume of gastric juice)×(acid concentration). The inhibition rate (%) was calculated according to the formula shown below. The results are shown in Table 1. The number of animals of each experimental group is four.

Inhibition rate (%)=100×(A−B)/A

A: acid output in solvent administered group
B: acid output in test compound administered group

TABLE 1

| Compound | Inhibition rate(%) |
| --- | --- |
| Example 1 | 79 |
| Example 2 | 86 |
| Example 3 | 85 |

Test Example 2

Measurement of Cytochrome P450 (CYP) Gene Induction in Human Cryopreserved Hepatocytes Human cryopreserved hepatocytes purchased from In Vitro Technology were quickly thawed at 37° C. After ice-cold William's E (WE) medium supplemented with 10% FCS, penicillin (100 U/mL), streptomycin (100 μg/mL) and glutamine (2 mM) (WE medium) was gradually added to hepatocytes, the cells were centrifuged at 500 rpm for 5 min at 4° C. The supernatant was removed and the cells were resuspended in WE medium to obtain 5×10$^5$ cells/mL. The cells were plated into collagen-coated 48-well plates (1×10$^5$ cells/cm$^2$) and cultured at 37° C. and 5% $CO_2$ for about 24 hr.

Medium was replaced with Hepato-STIM (trademark, BD Biosciences) supplemented with EGF, penicillin (100 U/mL), streptomycin (100 μg/mL) and glutamine (2 mM) (HS medium) and the cells were cultured for about 24 hr. At about 48 hr of culture after seeding, the cells were treated with the test compounds and β-naphtoflavone (β-NF, positive control for human CYP1A1 and CYP1A2, SIGMA) prepared by HS medium for about 48 hr. Medium was changed daily. The final concentration of β-NF was set to 10 μM. All compounds were dissolved in dimethylsulfoxide (DMSO, Wako), resulting in a final vehicle concentration of 0.1% (v/v). To the control cells, HS medium containing 0.1% DMSO was added.

After 48-hr exposure, cells were washed once using PBS, and total RNA was purified using Qiagen RNeasy Mini Kit (Qiagen) according to the manufacturer's instruction. Purified total RNA was then used as template for first strand cDNA synthesis. For reverse transcription (RT) reaction, Oligo dT was employed. The RT reaction was carried using TaqMan Reverse Transcription Reagents (Applied Biosystems) at 25° C. for 10 min followed by 60-min reaction at 48° C., and then the enzyme was inactivated at 95° C. for 5 min in Gene Amp PCR System 9700. The resulting cDNA was subjected to polymerase chain reaction (PCR) in ABI7700 Sequence Detection System (Applied Biosystems). For the mRNA analyses of CYP1A1 and GAPDH, SYBR Green PCR Core Reagents kit (Applied Biosystems) was used, and CYP1A2 mRNA was quantified using TaqMan PCR Core Reagents kit (Applied Biosystems). The forward (F) and reverse (R) primers for the analysis of each mRNA and PCR conditions used were shown in Tables 2 and 3-5, respectively.

TABLE 2

Primer Sequence (SEQ ID NOS.: 1-7)

| isozyme | GenBank# | primer | Name | sequence |
|---|---|---|---|---|
| CYP1A1 | XM_044663 | F | hCYP1A1_F1 | TGGTCTCCCTTCTCTACACTCTTGT |
| | | R | hCYP1A1_R1 | ATTTTCCCTATTACATTAAATCAATGGTTCT |
| CYP1A2 | AF_182274 | F | hCYP1A2_F12 | ACCATGACCCAGAGCTGTGG |
| | | R | hCYP1A2_R13 | TCACTCAAGGGCTTGTTAAT |
| | | Probe (FAM/TAMRA) | hCYP1A2_probe1 | AGGACCCCTCTGAGTTCCGGCCT |
| GAPDH | M_33197 | F | hGAPDH_F | GAAGGTGAAGGTCGGAGTC |
| | | R | hGAPDH_R | GAAGATGGTGATGGGATTTC |

PCR Conditions

TABLE 3

| GAPDH | | |
|---|---|---|
| Temperature | Time | |
| 95 | 10 min | |
| 94 | 15 s | denaturation |
| 56 | 15 s | annealing |
| 72 | 30 s | extension |

40 cycles

TABLE 4

| CYP1A1 | | |
|---|---|---|
| Temperature | Time | |
| 95 | 10 min | |
| 94 | 15 s | denaturation |
| 56 | 15 s | annealing |
| 72 | 30 s | extension |

50 cycles

TABLE 5

| CYP1A2 | | |
|---|---|---|
| Temperature | Time | |
| 95 | 10 min | |
| 94 | 15 s | denaturation |
| 58 | 15 s | annealing |
| 72 | 30 s | extension |

50 cycles

<Data Analysis>

Data analysis was performed as follows. The amount of mRNA of CYP1A1 or CYP1A2 was divided by that of GAPDH. Then, the ratio (fold) of the values obtained in test compounds (X) and positive control (P) against that in control was calculated. The induction potency of test compound (%) was obtained by following equation:

Induction potency of test compound (%)= $100 \times (X-1)/(P-1)$

<Results>

In Test Example 2, to assess CYP induction in liver, which is one of the problems in the development of new drug, induction of mRNAs of CYP1A isozymes was studied using human cryopreserved hepatocytes. As the results, test compound showed week induction potency, resulted in less than 12% at 3 uM and less than 30% at 10 uM as compared with positive control (100%).

TABLE 6

| Sample | Conc. | CYP1A1 | CYP1A2 |
|---|---|---|---|
| Control | 0.1% DMSO | (1.00) | (1.00) |
| βNF | 10 μM | 100 (79.97) | 100 (14.16) |
| Example 1 | 0.3 μM | 2.03 | 8.36 |
| Example 1 | 1 μM | 8.02 | 12.16 |
| Example 1 | 3 μM | 11.27 | 11.78 |
| Example 1 | 10 μM | 18.46 | 29.18 |

Each value in Table 6 represents the % of the positive control (100%). Figures in parentheses show the fold induction by positive control as compared with control.

INDUSTRIAL APPLICABILITY

Since the compound of the present invention has an excellent gastric acid secretion inhibitory activity, higher safety and more suitable physicochemical stability, it can serve as a drug particularly useful for acid related diseases.

[Sequence Listing Free Text]

SEQ ID No. 1: Primer F
SEQ ID No. 2: Primer R
SEQ ID No. 3: Primer F
SEQ ID No. 4: Primer R
SEQ ID No. 5: Probe (FAM/TAMRA)
SEQ ID No. 6: Primer F
SEQ ID No. 7: Primer R

The invention claimed is:

1. A compound represented by the following formula (1), or a salt thereof:

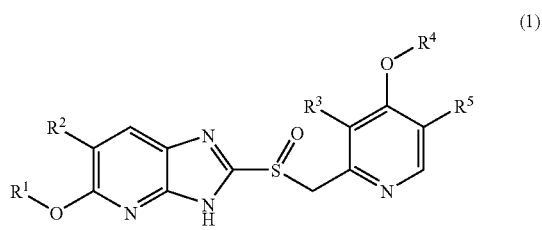

wherein $R^1$ represents a C2-C6 alkynyl group, or a phenyl group optionally having a substituent of a halogen atom or a C1-C6 alkoxy group;
$R^2$ represents a methyl group;
$R^3$ represents a methyl or ethyl group;
$R^4$ represents a C1-C6 alkyl group; and
$R^5$ represents a hydrogen atom.

2. The compound or a salt thereof according to claim 1, wherein $R^1$ is a C2-C6 alkynyl group.

3. The compound or a salt thereof according to claim 1, wherein $R^1$ is a phenyl group optionally having a substituent of a halogen atom or a C1-C6 alkoxy group.

4. 5-(4-Fluorophenoxy)-2-(((4-methoxy-3-methyl-2-pyridinyl)methyl)sulfinyl)-3H-imidazo[4,5-b]pyridine.

5. 5-(3-Fluorophenoxy)-2-(((4-methoxy-3-methyl-2-pyridinyl)methyl)sulfinyl)-3H-imidazo[4,5-b]pyridine.

6. 2-(((4-Methoxy-3-methyl-2-pyridinyl)methyl)sulfinyl)-5-(4-methoxyphenoxy)-6-methyl-3H-imidazo[4,5-b]pyridine.

7. 5-(2-Butynyloxy)-2-(((4-methoxy-3-methyl-2-pyridinyl)methyl)sulfinyl)-6-methyl-3H-imidazo[4,5-b]pyridine.

8. 2-[[(4-Methoxy-3-methyl-2-pyridinyl)methyl]sulfinyl]-5-(3-pentynyloxy)-3H-imidazo[4,5-b]pyridine.

9. 5-(2-Butynyloxy)-2-[[(4-methoxy-3-methyl-2-pyridinyl)methyl]sulfinyl]-3H-imidazo[4,5-b]pyridine.

10. Sodium salt of 5-(4-fluorophenoxy)-2-(((4-methoxy-3-methyl-2-pyridinyl)methyl)sulfinyl)-3H-imidazo[4,5-b]pyridine.

11. Sodium salt of 5-(3-fluorophenoxy)-2-(((4-methoxy-3-methyl-2-pyridinyl)methyl)sulfinyl)-3H-imidazo[4,5-b]pyridine.

12. Sodium salt of 2-(((4-methoxy-3-methyl-2-pyridinyl)methyl)sulfinyl)-5-(4-methoxyphenoxy)-6-methyl-3H-imidazo[4,5-b]pyridine.

13. Sodium salt of 5-(2-butynyloxy)-2-(((4-methoxy-3-methyl-2-pyridinyl)methyl)sulfinyl)-6-methyl-3H-imidazo[4,5-b]pyridine.

14. 2-[[(4-Methoxy-3-methyl-2-pyridinyl)methyl]sulfinyl]-5-(3-pentynyloxy)-3H-imidazo[4,5-b]pyridine sodium salt.

15. 5-(2-Butynyloxy)-2-[[(4-methoxy-3-methyl-2-pyridinyl)methyl]sulfinyl]-3H-imidazo[4,5-b]pyridine sodium salt.

* * * * *

SEQUENCE LISTING

<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: Synthetic PCR primer F
<220> FEATURE:
<221> NAME/KEY: primer_bind
<222> LOCATION: (1)..(25)

<400> SEQUENCE: 1
tggtctccct tctctacact cttgt                                              25

<210> SEQ ID NO 2
<211> LENGTH: 31
<212> TYPE: DNA
<213> ORGANISM: Artificial Sequence
<220> FEATURE:
<223> OTHER INFORMATION: Synthetic PCR primer R
<220> FEATURE:
<221> NAME/KEY: primer_bind
<222> LOCATION: (1)..(31)

<400> SEQUENCE: 2
attttcccta ttacattaaa tcaatggttc t                                       31

<210> SEQ ID NO 3
<211> LENGTH: 20
<212> TYPE: DNA
<213> ORGANISM: Artificial Sequence
<220> FEATURE:
<223> OTHER INFORMATION: Synthetic PCR primer F
<220> FEATURE:
<221> NAME/KEY: primer_bind
<222> LOCATION: (1)..(20)

<400> SEQUENCE: 3
accatgaccc agagctgtgg                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic PCR primer R
<220> FEATURE:
<221> NAME/KEY: primer_bind
<222> LOCATION: (1)..(20)

<400> SEQUENCE: 4
tcactcaagg gcttgttaat                                                    20

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide probe(FAM/TAMRA)
<220> FEATURE:
<221> NAME/KEY: primer_bind
<222> LOCATION: (1)..(23)

<400> SEQUENCE: 5
aggacccctc tgagttccgg cct                                                23

```
<210> SEQ ID NO 6
<211> LENGTH: 19
<212> TYPE: DNA
<213> ORGANISM: Artificial Sequence
<220> FEATURE:
<223> OTHER INFORMATION: Synthetic PCR primer F
<220> FEATURE:
<221> NAME/KEY: primer_bind
<222> LOCATION: (1)..(19)

<400> SEQUENCE: 6
gaaggtgaag gtcggagtc                                              19

<210> SEQ ID NO 7
<211> LENGTH: 20
<212> TYPE: DNA
<213> ORGANISM: Artificial Sequence
<220> FEATURE:
<223> OTHER INFORMATION: Synthetic PCR primer R

<400> SEQUENCE: 7
gaagatggtg atgggatttc                                             20
```